(12) United States Patent
Kim et al.

(10) Patent No.: US 12,305,193 B2
(45) Date of Patent: *May 20, 2025

(54) THREE-DIMENSIONAL MICRO-ENVIRONMENT STRUCTURE FOR CONTROLLING CELL BEHAVIOR, THREE-DIMENSIONAL SURFACE FOR CONTROLLING CELL BEHAVIOR, AND METHOD FOR MANUFACTURING ARRAY AND THREE-DIMENSIONAL MICRO-ENVIRONMENT STRUCTURE

(71) Applicants: Amolifescience Co., Ltd., Seoul (KR); Kollodis BioSciences, Inc., North Augusta, SC (US)

(72) Inventors: Chan Kim, Gwangju (KR); Kyu-Won Baek, Seoul (KR); Hui-Gwan Goo, Seoul (KR); Sang-Jae Lee, Seoul (KR); Bong-Jin Hong, Pohang-si (KR); Song-Hee Koo, Seoul (KR); In-Yong Seo, Seoul (KR); Seung-Hoon Lee, Paju-si (KR); Ji-Hyun Lee, Incheon (KR); Seon-Ho Jang, Seoul (KR); Dong-Sik Seo, Incheon (KR)

(73) Assignees: Amolifescience Co., Ltd., Seoul (KR); Kollodis BioSciences, Inc., North Augusta, SC (US)

( * ) Notice: Subject to any disclaimer, the term of this patent is extended or adjusted under 35 U.S.C. 154(b) by 1227 days.

This patent is subject to a terminal disclaimer.

(21) Appl. No.: 16/467,613

(22) PCT Filed: Dec. 7, 2016

(86) PCT No.: PCT/KR2016/014319
§ 371 (c)(1),
(2) Date: Sep. 6, 2019

(87) PCT Pub. No.: WO2018/105777
PCT Pub. Date: Jun. 14, 2018

(65) Prior Publication Data
US 2019/0382719 A1 Dec. 19, 2019

(51) Int. Cl.
| | | |
|---|---|---|
| *C12N 5/00* | (2006.01) |
| *A61K 38/10* | (2006.01) |
| *A61K 38/16* | (2006.01) |
| *C07K 14/485* | (2006.01) |
| *C07K 14/495* | (2006.01) |
| *C07K 14/50* | (2006.01) |
| *C07K 14/54* | (2006.01) |
| *C08J 3/075* | (2006.01) |

(52) U.S. Cl.
CPC ............ *C12N 5/0068* (2013.01); *A61K 38/10* (2013.01); *A61K 38/16* (2013.01); *C07K 14/485* (2013.01); *C07K 14/495* (2013.01); *C07K 14/50* (2013.01); *C07K 14/5415* (2013.01); *C08J 3/075* (2013.01); *C08J 2371/02* (2013.01); *C08J 2471/02* (2013.01); *C12N 2533/30* (2013.01)

(58) Field of Classification Search
None
See application file for complete search history.

(56) References Cited

U.S. PATENT DOCUMENTS

| | | | |
|---|---|---|---|
| 9,868,828 B2 * | 1/2018 | Cho | ............................ C08J 3/28 |
| 11,220,669 B2 * | 1/2022 | Kim | ...................... C12N 5/0062 |
| 2005/0095695 A1 | 5/2005 | Schindler et al. |
| 2007/0231362 A1 | 10/2007 | Perez et al. |
| 2010/0297768 A1 | 11/2010 | Schindler et al. |
| 2015/0030681 A1 | 1/2015 | Merry et al. |

FOREIGN PATENT DOCUMENTS

| | | | | |
|---|---|---|---|---|
| AU | 2016431869 A1 | 7/2019 | | |
| JP | 2007-510820 A | 4/2007 | | |
| JP | 2009-532070 A | 9/2009 | | |
| JP | 2010-207228 A | 9/2010 | | |
| JP | 2015-528493 A | 9/2015 | | |
| KR | 10-1311325 B1 | 9/2013 | | |
| WO | WO-9503821 A1 * | 2/1995 | ............. | A61K 38/18 |
| WO | WO-2008093646 A1 * | 8/2008 | ............. | A61P 25/00 |
| WO | WO 2011/115420 A2 | 9/2011 | | |
| WO | WO 2014/034146 A1 | 3/2014 | | |
| WO | WO-2014042463 A1 * | 3/2014 | ........... | A61L 27/227 |

OTHER PUBLICATIONS

Krammer et al., Matrix Biol. 21:139-147 (2002) (Year: 2002).*
Kollodis Biosciences, "An ECM Mimetic Library for Engineering Surfaces to Direct Cell Surface Receptor Binding Specificity and Signaling," available online at www.kollodis.com/down/MAPTrixECMLibrary.pdf, 1 page (2012) (Year: 2012).*
Li et al., Proc. Natl. Acad. Sci. USA 108:11745-11750 (2011) (Year: 2011).*
English language machine translation of WO 2008/093646 A1 (accessed on Mar. 21, 2024) (Year: 2024).*
Japanese Office Action for JP Application No. 2019-531304, mailed Mar. 30, 2021.
Extended European Search Report for Application No. EP16923489.5 mailed Jan. 17, 2020.
Lee et al., Engineering integrin signaling for promoting embryonic stem cell self-renewal in a precisely defined niche. Biomaterials. Feb. 2010;31(6):1219-26. doi: 10.1016/j.biomaterials.2009.10.054. Epub Nov. 18, 2009.

(Continued)

*Primary Examiner* — Thea D'Ambrosio
(74) *Attorney, Agent, or Firm* — Wolf, Greenfield & Sacks, P.C.

(57) ABSTRACT

The present disclosure relates to a three-dimensional micro-environment structure for controlling cell behavior, a three-dimensional surface and an array for controlling cell behavior, and a method for manufacturing the three-dimensional micro-environment structure.

4 Claims, 23 Drawing Sheets

Specification includes a Sequence Listing.

(56) References Cited

OTHER PUBLICATIONS

Reyes et al., Mixed extracellular matrix ligands synergistically modulate integrin adhesion and signaling. J Cell Physiol. Nov. 2008;217(2):450-8. doi: 10.1002/jcp.21512.
International Search Report and Written Opinion for Application No. PCT/KR2016/014319 mailed Aug. 29, 2017.
International Preliminary Report on Patentability for Application No. PCT/KR2016/014319 mailed Jun. 11, 2019.
Koutsopoulos, Self-assembling peptide nanofiber hydrogels in tissue engineering and regenerative medicine: Progress, design guidelines, and applications. J Biomed Mater Res A. Apr. 2016;104(4):1002-16. doi: 10.1002/jbm.a.35638. Epub Jan. 25, 2016.
Shin et al., Biomimetic Hybrid Nanofiber Sheets Composed of RGD Peptide-Decorated PLGA as Cell-Adhesive Substrates. J Funct Biomater. May 29, 2015;6(2):367-78.
Amsbio, An ECM mimetic library for engineering surfaces to direct cell surface receptor binding specificity and signaling. 2012. 8 pages.

* cited by examiner

[FIG. 1]
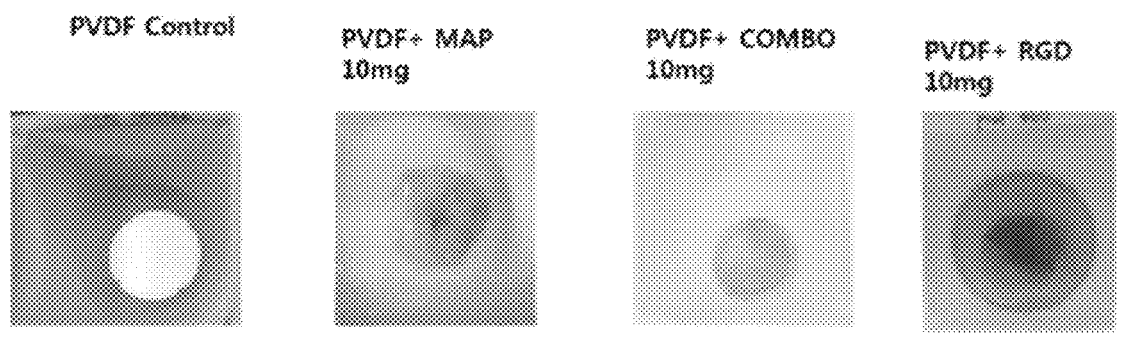

[FIG. 2A]
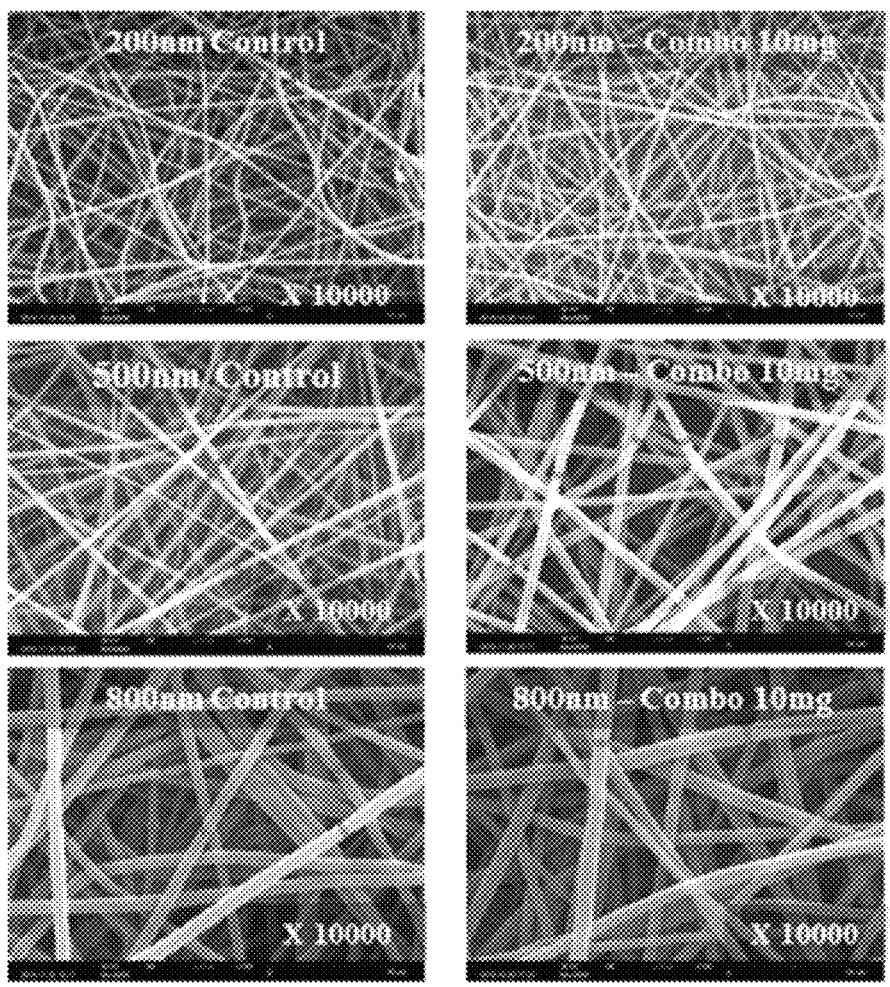

[FIG. 2B]
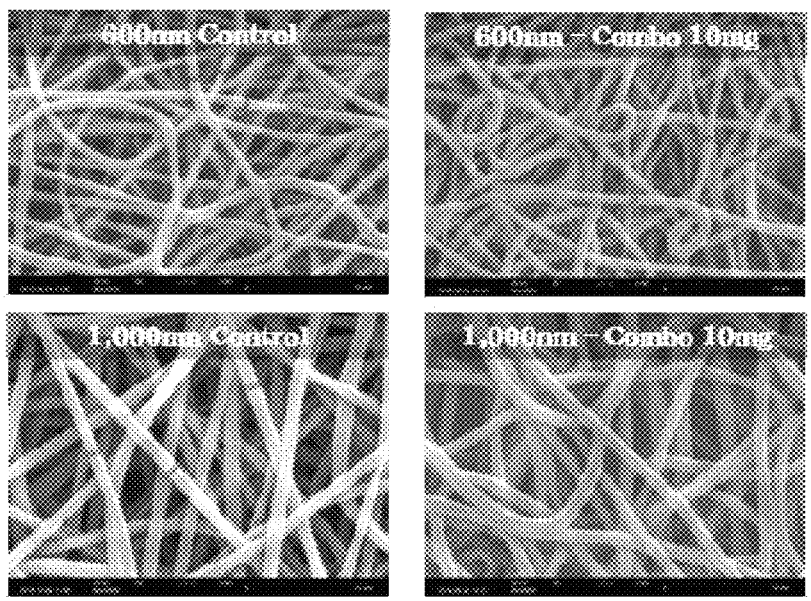
[FIG. 3]
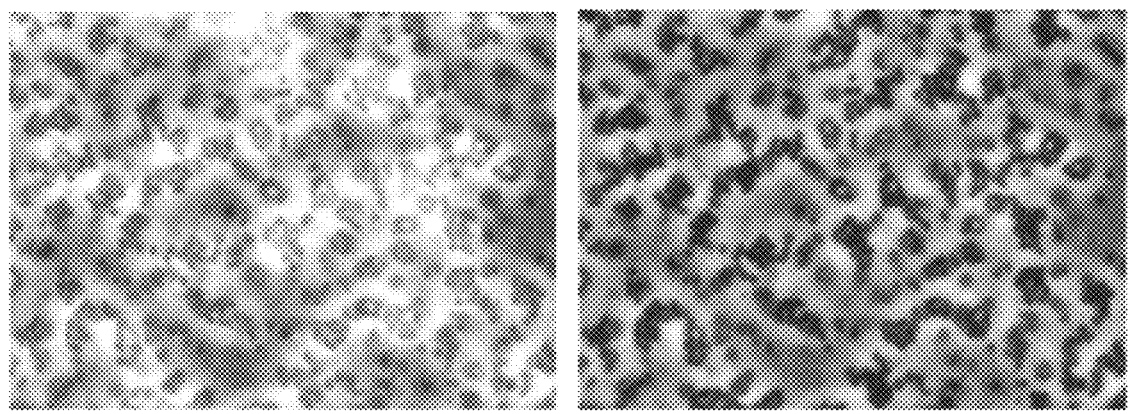

[FIG. 4]
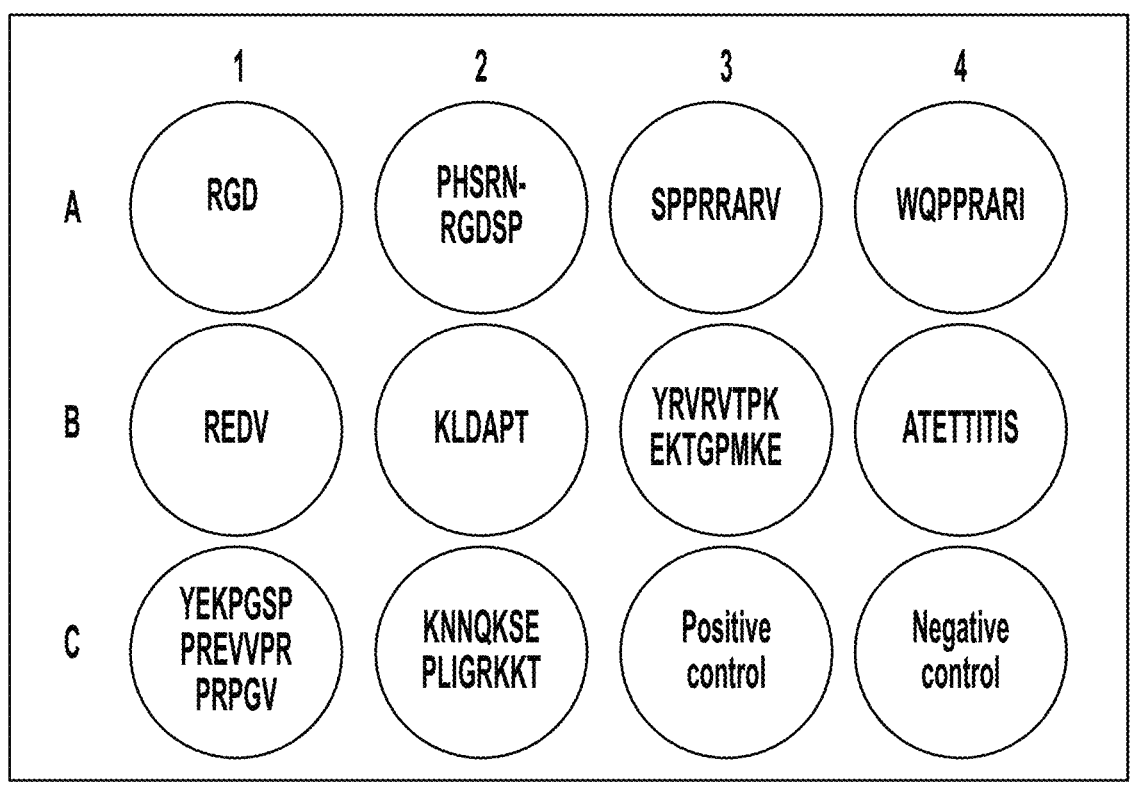

[FIG. 5]
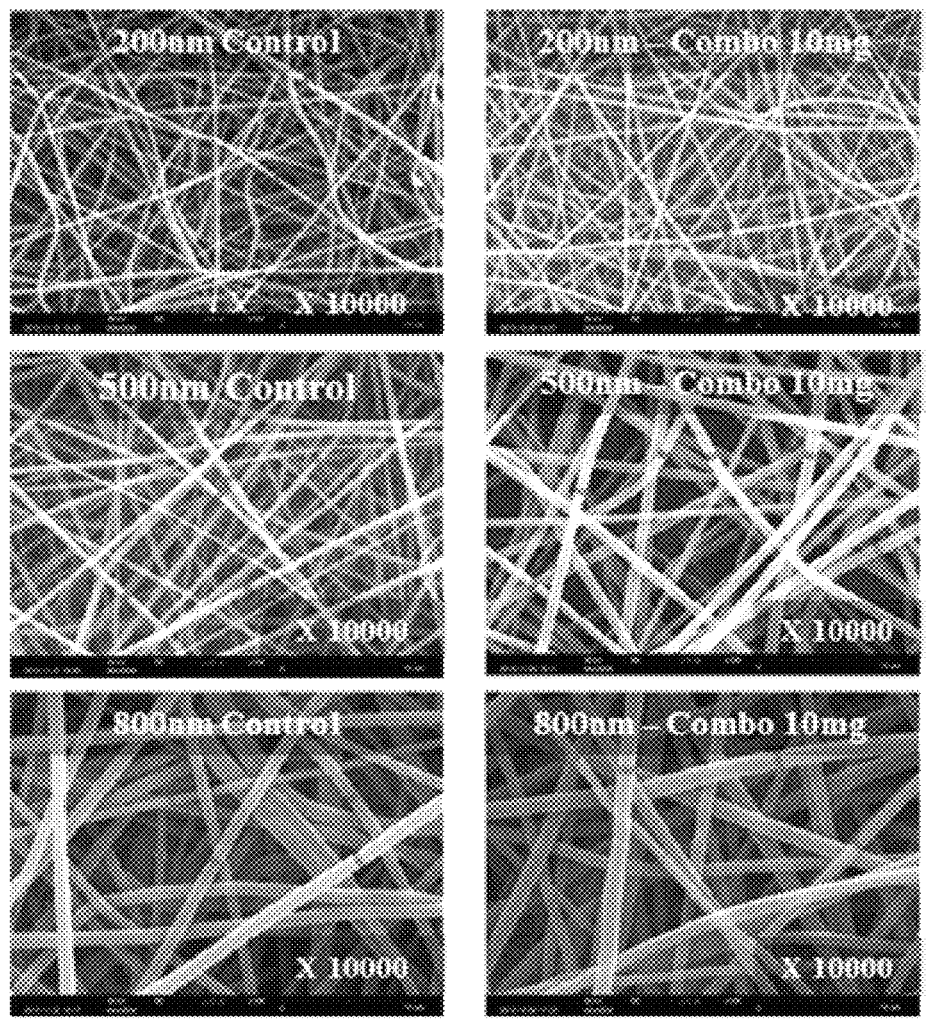

[FIG. 6A]
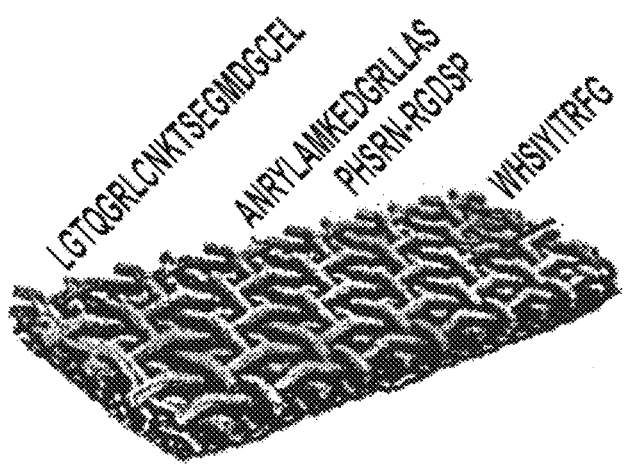
[FIG. 6B]
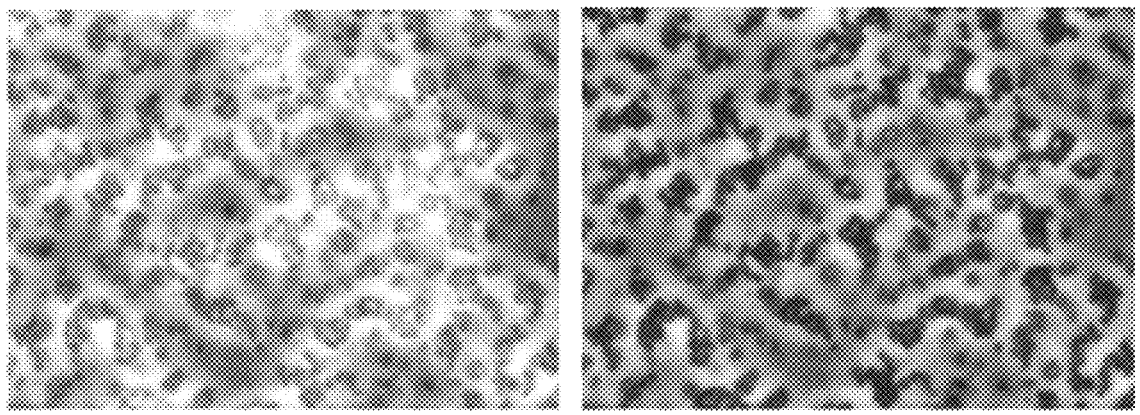

[FIG. 6C]
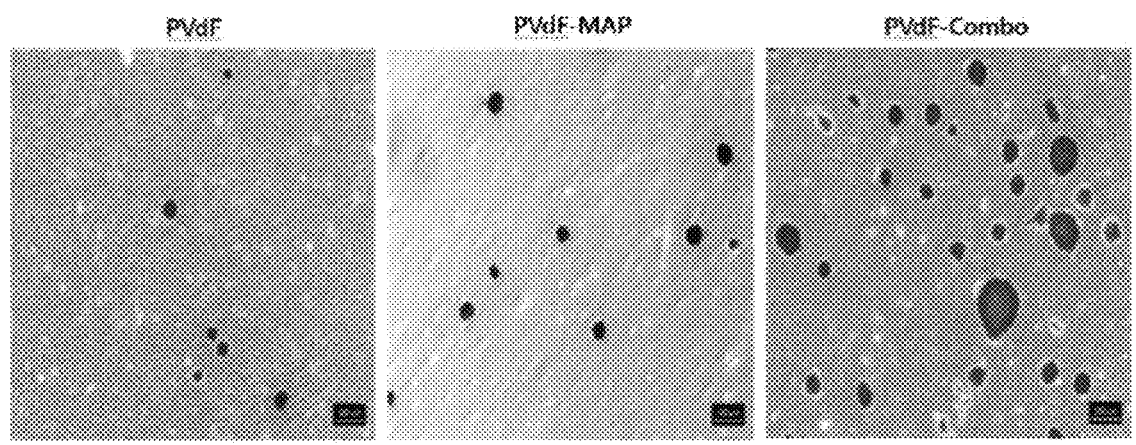

[FIG. 7]

|   | 1 | 2 | 3 | 4 |
|---|---|---|---|---|
| A | Matrigel (positive control) | MAP (negative control) | RGD (αVβ3) | PHSRN-RGDSP (α5β1) |
| B | SPPRRARVT (heparin) | TWYKIAFQRNRK (α6β1) | RKRLQVQLSIRT (α6β1) | NRWHSIYITRFG (α6β1) |
| C | LCCGRGHRTRTQRVTERCNC (frizzed receptor) | LGTQGRLCNKTSEGMDGCEL (frizzed receptor) | IVPLLLLVLH (LIF receptor) | YTAQGEPFPNNVEKLCAP (LIF receptor) |

[FIG. 8]

[FIG. 9]
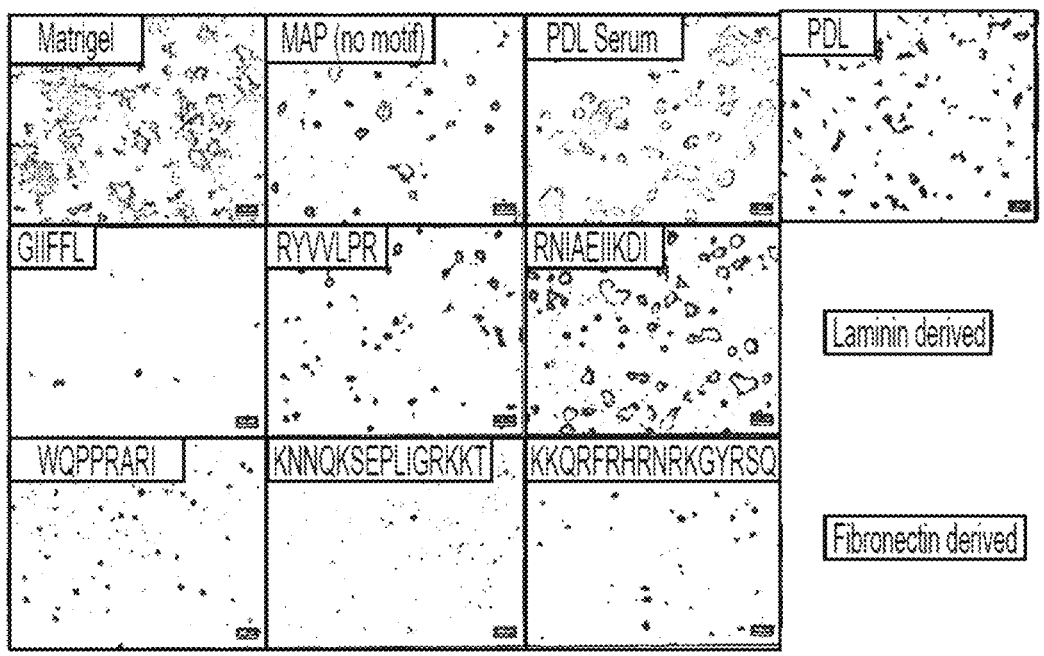

[FIG. 10A]

Cadherin derived

[FIG. 11]
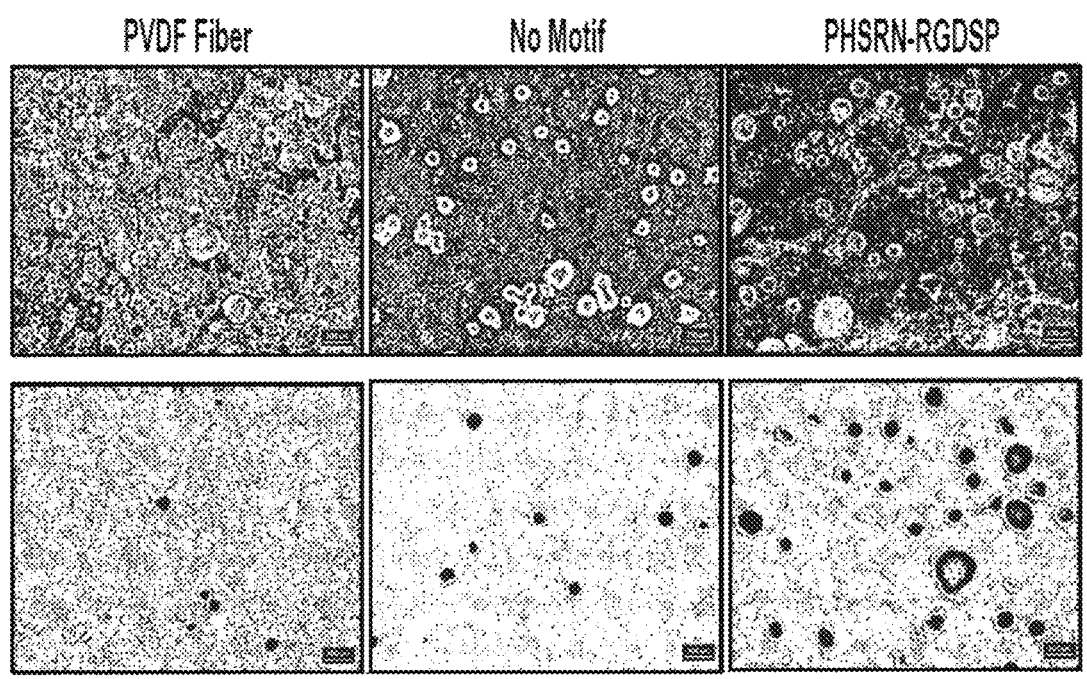

[FIG. 12]
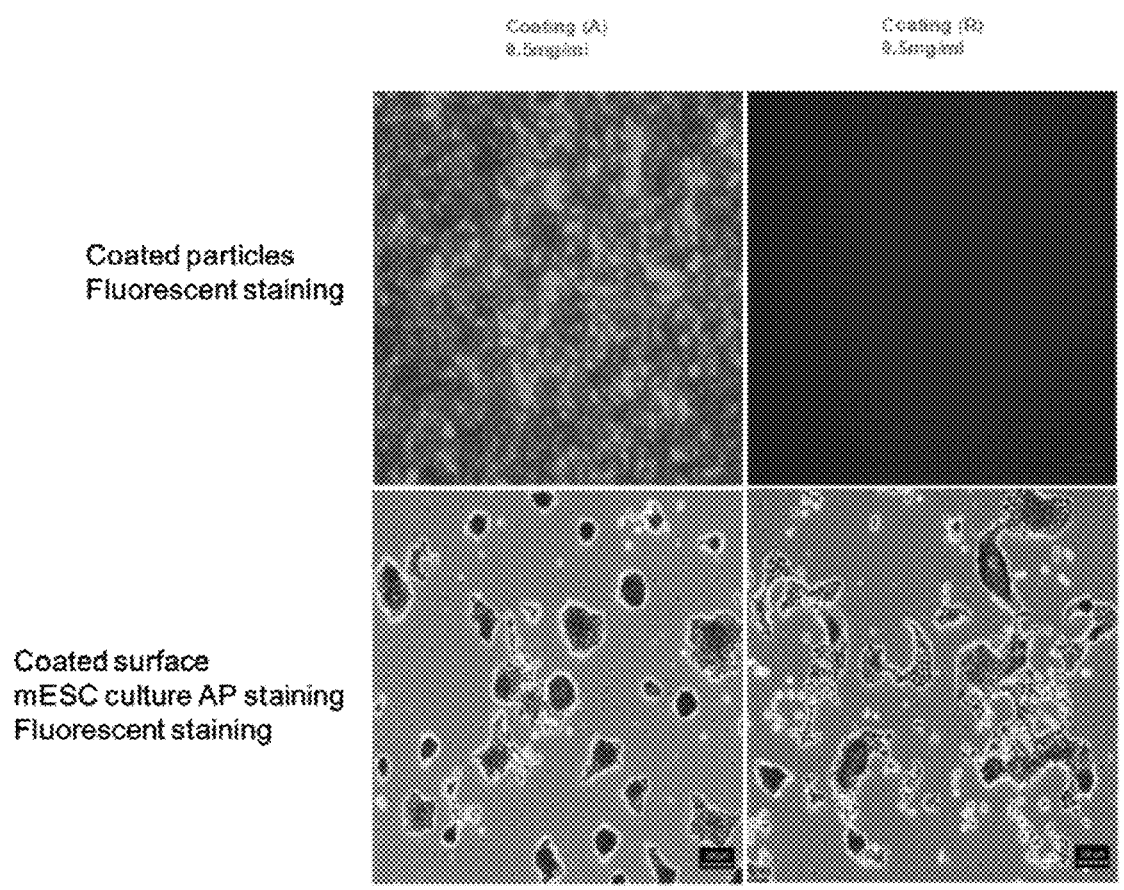

[FIG. 13]
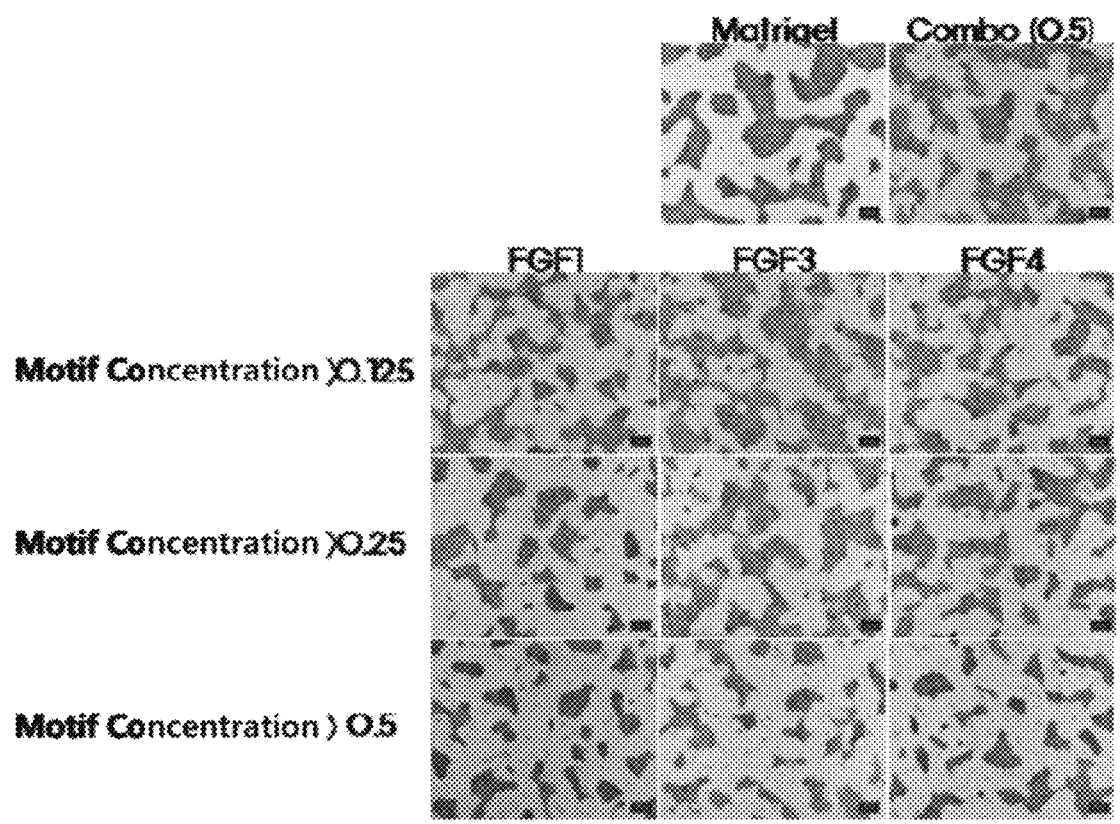

[FIG. 14A]
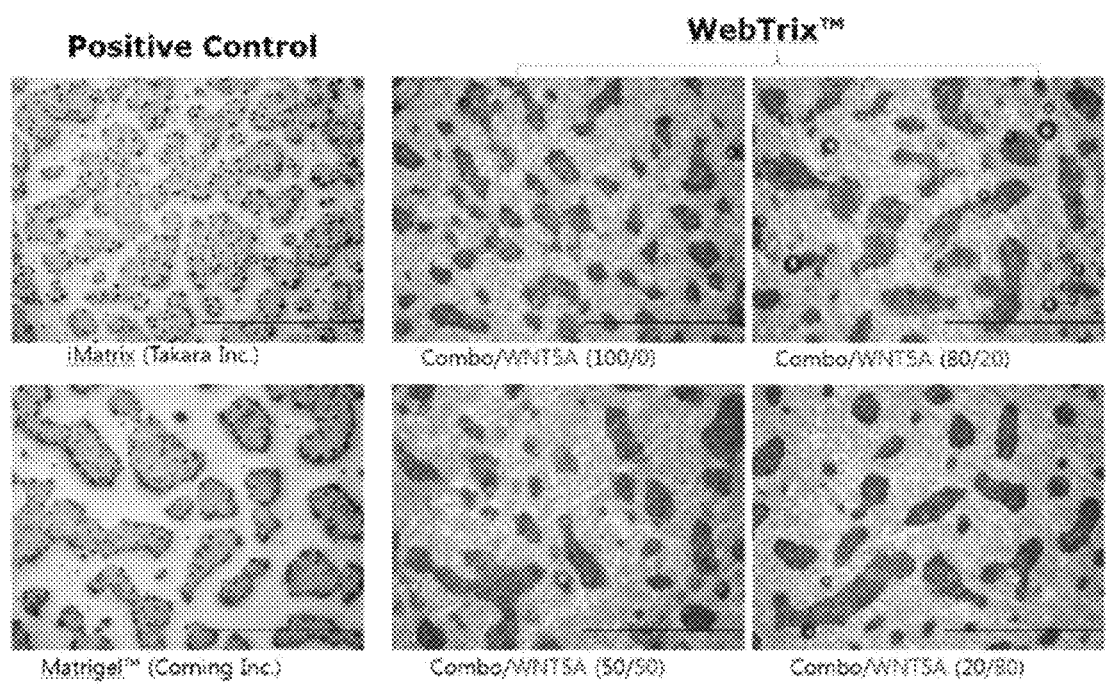

[FIG. 14B]
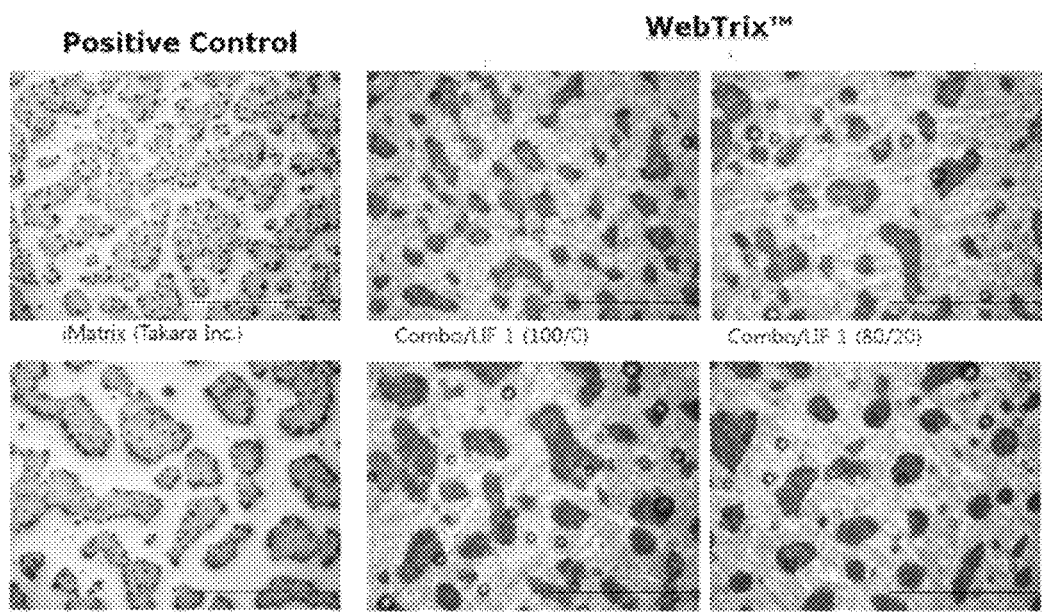
[FIG. 15]
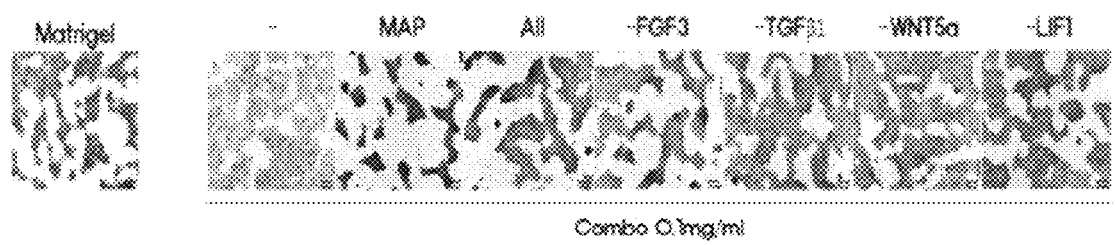

[FIG. 16]
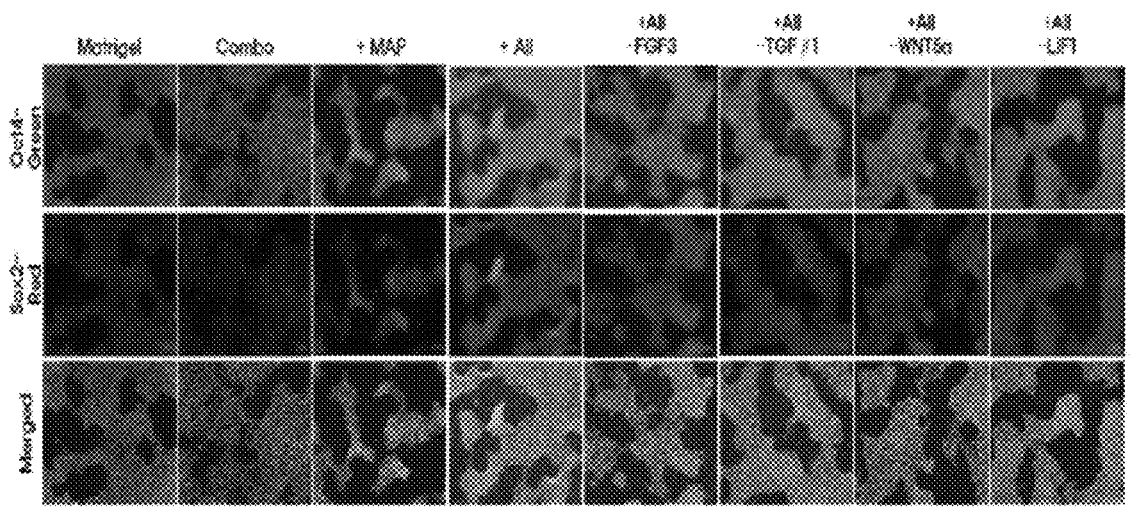

[FIG. 17]
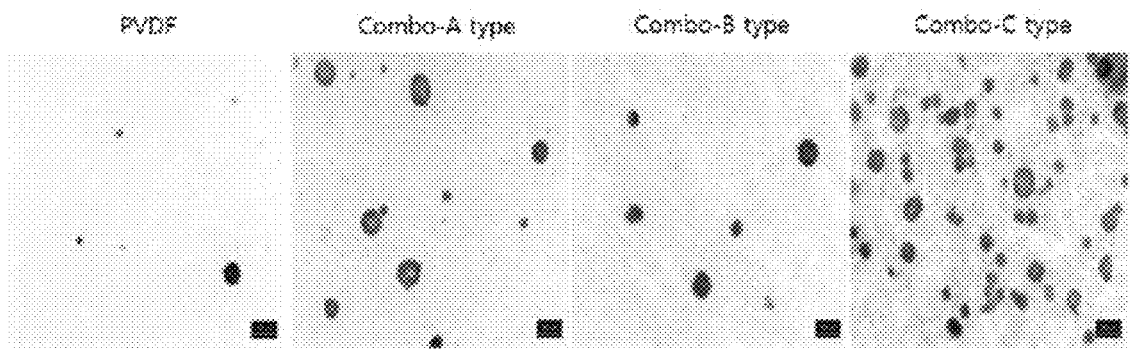
[FIG. 18]
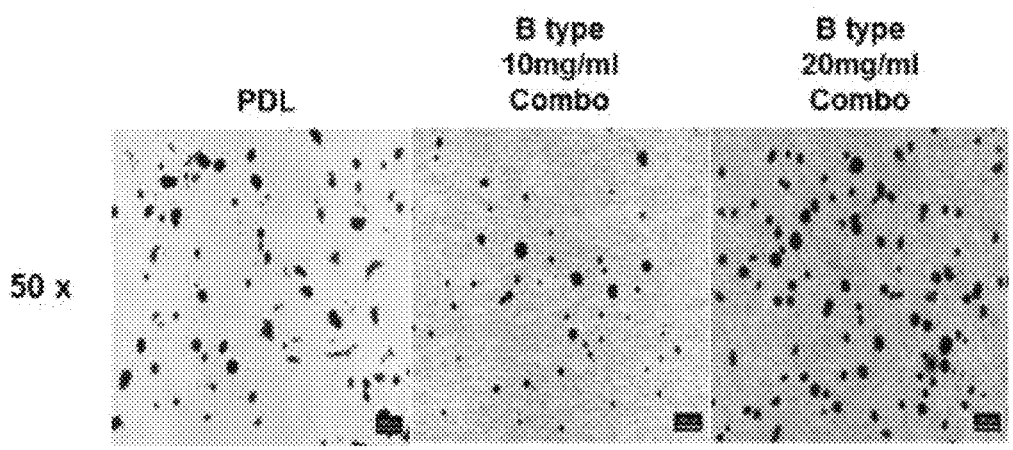

[FIG. 19]
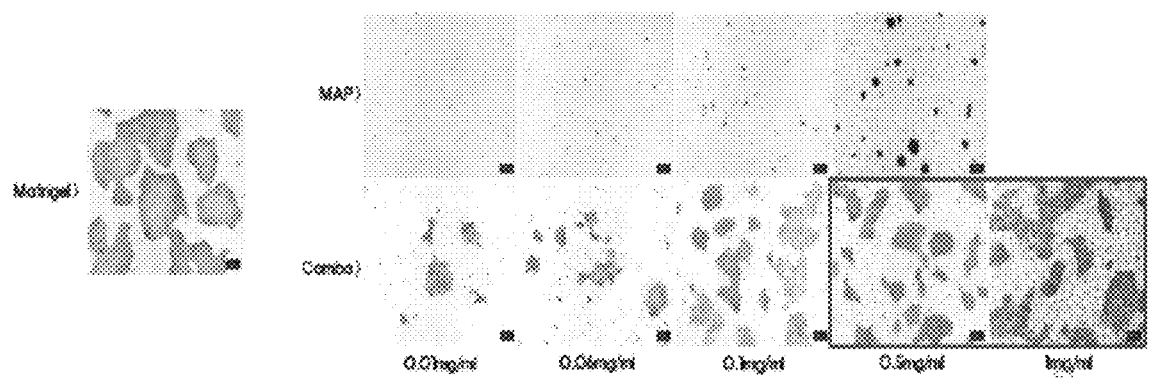
[FIG. 20]
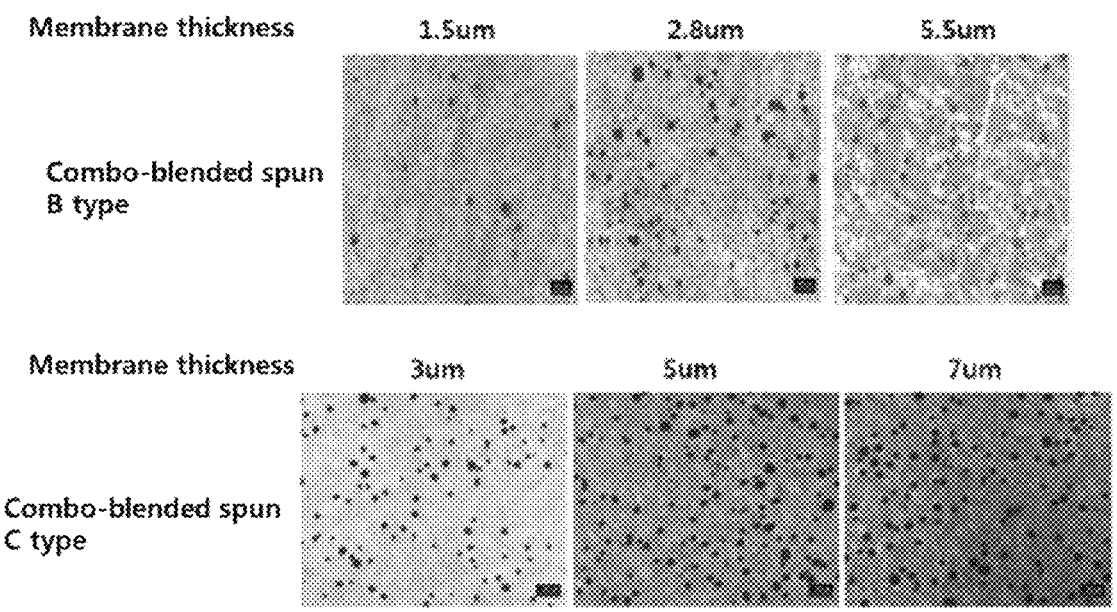

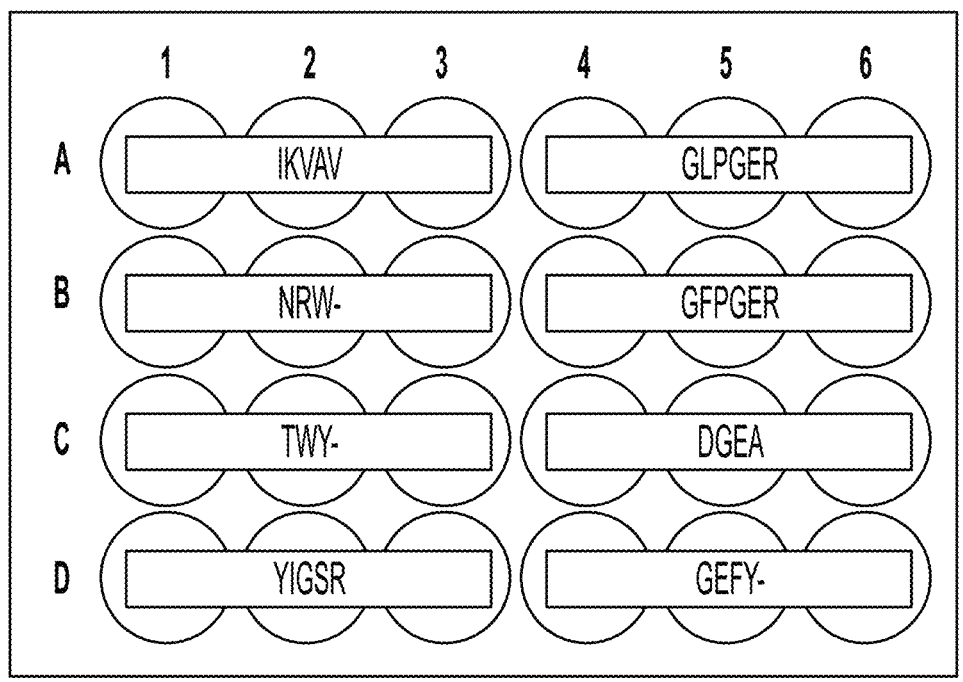
[FIG. 21]

[FIG. 22]
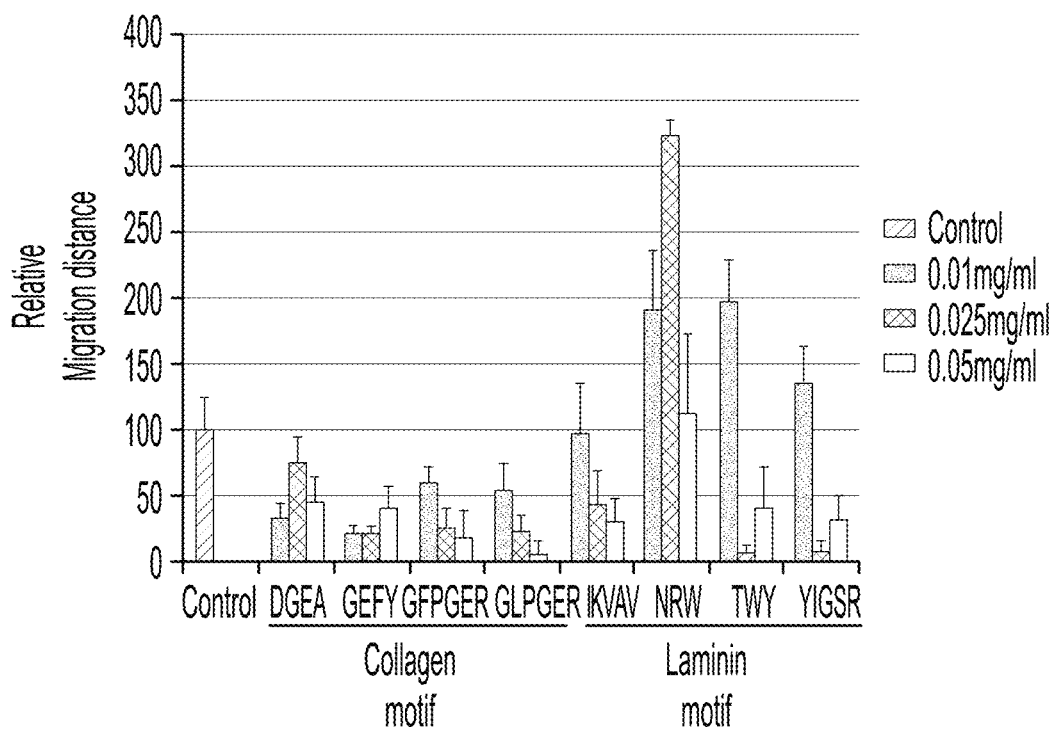
[FIG. 23A]
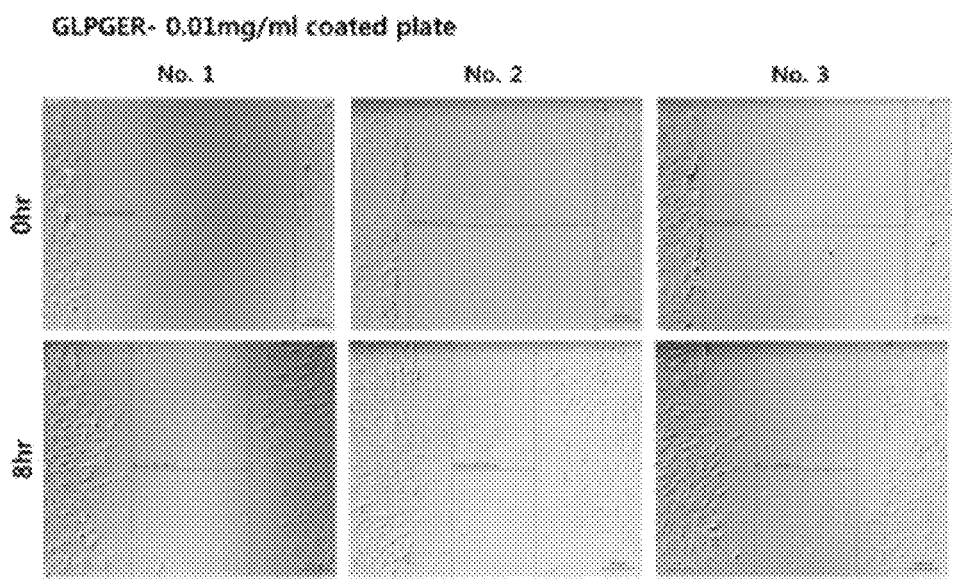
GLPGER- 0.01mg/ml coated plate

[FIG. 23B]
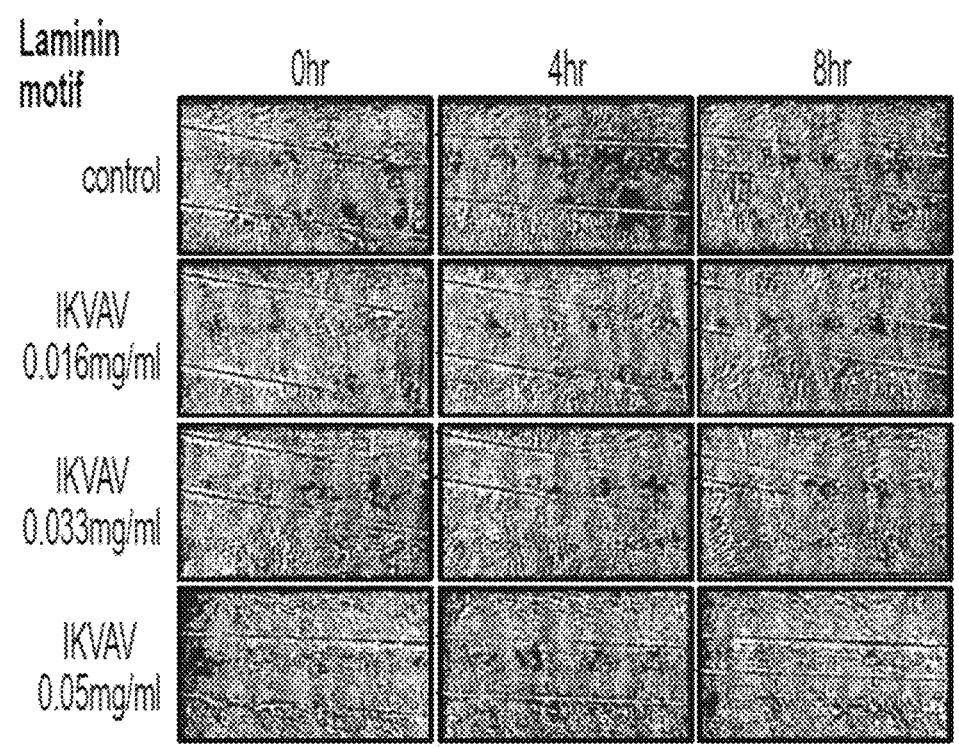

[FIG. 24]
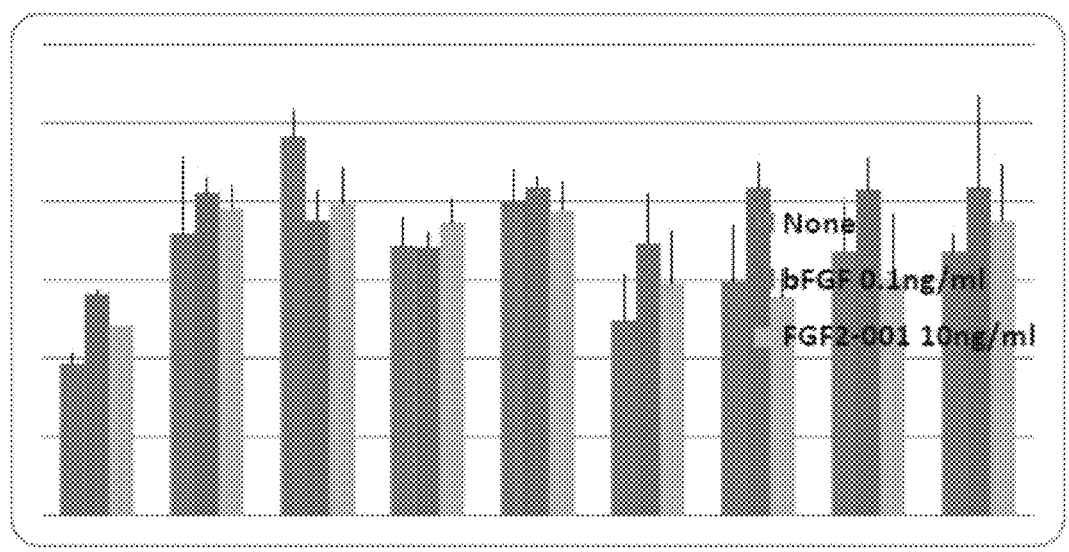

SEQUENCE LISTING

<160> NUMBER OF SEQ ID NOS: 72

<210> SEQ ID NO 1

-continued

```
<211> LENGTH: 10
<212> TYPE: PRT
<213> ORGANISM: Mytilus edulis

<400> SEQUENCE: 1

Ala Lys Pro Ser Tyr Pro Pro Thr Tyr Lys
1               5                   10

<210> SEQ ID NO 2
<211> LENGTH: 20
<212> TYPE: PRT
<213> ORGANISM: Mytilus edulis

<400> SEQUENCE: 2

Ala Lys Pro Ser Tyr Pro Pro Thr Tyr Lys Ala Lys Pro Ser Tyr Pro
1               5                   10                  15

Pro Thr Tyr Lys
            20

<210> SEQ ID NO 3
<211> LENGTH: 60
<212> TYPE: PRT
<213> ORGANISM: Mytilus edulis

<400> SEQUENCE: 3

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60

<210> SEQ ID NO 4
<211> LENGTH: 39
<212> TYPE: PRT
<213> ORGANISM: Mytilus californianus

<400> SEQUENCE: 4

Glu Val His Ala Cys Lys Pro Asn Pro Cys Lys Asn Asn Gly Arg Cys
1               5                   10                  15

Tyr Pro Asp Gly Lys Thr Gly Tyr Lys Cys Lys Cys Val Gly Gly Tyr
            20                  25                  30

Ser Gly Pro Thr Cys Ala Cys
        35

<210> SEQ ID NO 5
<211> LENGTH: 52
<212> TYPE: PRT
<213> ORGANISM: Mytilus edulis

<400> SEQUENCE: 5

Ala Asp Tyr Tyr Gly Pro Lys Tyr Gly Pro Pro Arg Arg Tyr Gly Gly
1               5                   10                  15

Gly Asn Tyr Asn Arg Tyr Gly Gly Ser Arg Arg Tyr Gly Gly Tyr Lys
            20                  25                  30

Gly Trp Asn Asn Gly Trp Lys Arg Gly Arg Trp Gly Arg Lys Tyr Tyr
        35                  40                  45

Glu Phe Glu Phe
    50
```

<210> SEQ ID NO 6
<211> LENGTH: 46
<212> TYPE: PRT
<213> ORGANISM: Mytilus galloprovincialis

<400> SEQUENCE: 6

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

<210> SEQ ID NO 7
<211> LENGTH: 60
<212> TYPE: PRT
<213> ORGANISM: Mytilus californianus

<400> SEQUENCE: 7

Gly His Val His Arg His Arg Val Leu His Lys His Val His Asn His
1               5                   10                  15

Arg Val Leu His Lys His Leu His Lys His Gln Val Leu His Gly His
            20                  25                  30

Val His Arg His Gln Val Leu His Lys His Val His Asn His Arg Val
        35                  40                  45

Leu His Lys His Leu His Lys His Gln Val Leu His
    50                  55                  60

<210> SEQ ID NO 8
<211> LENGTH: 75
<212> TYPE: PRT
<213> ORGANISM: Mytilus edulis

<400> SEQUENCE: 8

Ser Ser Glu Glu Tyr Lys Gly Gly Tyr Tyr Pro Gly Asn Ala Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Ser Ser
65                  70                  75

<210> SEQ ID NO 9
<211> LENGTH: 76
<212> TYPE: PRT
<213> ORGANISM: Mytilus edulis

<400> SEQUENCE: 9

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Lys Tyr Lys
        35                  40                  45

Asn Ser Gly Lys Tyr Lys Tyr Leu Lys Lys Ala Arg Lys Tyr His Arg

```
                    50                  55                  60

Lys Gly Tyr Lys Lys Tyr Tyr Gly Gly Gly Ser Ser
 65                  70                  75

<210> SEQ ID NO 10
<211> LENGTH: 71
<212> TYPE: PRT
<213> ORGANISM: Mytilus coruscus

<400> SEQUENCE: 10

Tyr Asp Asp Tyr Ser Asp Gly Tyr Tyr Pro Gly Ser Ala Tyr Asn Tyr
  1               5                  10                  15

Pro Ser Gly Ser His Trp His Gly His Gly Tyr Lys Gly Lys Tyr Tyr
                 20                  25                  30

Gly Lys Gly Lys Lys Tyr Tyr Lys Phe Lys Arg Thr Gly Lys Tyr
             35                  40                  45

Lys Tyr Leu Lys Lys Ala Arg Lys Tyr His Arg Lys Gly Tyr Lys Lys
         50                  55                  60

His Tyr Gly Gly Ser Ser Ser
 65                  70

<210> SEQ ID NO 11
<211> LENGTH: 76
<212> TYPE: PRT
<213> ORGANISM: Mytilus galloprovincialis

<400> SEQUENCE: 11

Ser Ser Glu Glu Tyr Lys Gly Gly Tyr Tyr Pro Gly Asn Thr Tyr His
  1               5                  10                  15

Tyr His Ser Gly Gly Ser Tyr His Gly Ser Gly Tyr His Gly Gly Tyr
                 20                  25                  30

Lys Gly Lys Tyr Tyr Gly Lys Ala Lys Tyr Tyr Lys Tyr Lys
             35                  40                  45

Asn Ser Gly Lys Tyr Lys Tyr Leu Lys Lys Ala Arg Lys Tyr His Arg
         50                  55                  60

Lys Gly Tyr Lys Lys Tyr Tyr Gly Gly Gly Ser Ser
 65                  70                  75

<210> SEQ ID NO 12
<211> LENGTH: 99
<212> TYPE: PRT
<213> ORGANISM: Mytilus edulis

<400> SEQUENCE: 12

Gly Gly Gly Asn Tyr Arg Gly Tyr Cys Ser Asn Lys Gly Cys Arg Ser
  1               5                  10                  15

Gly Tyr Ile Phe Tyr Asp Asn Arg Gly Phe Cys Lys Tyr Gly Ser Ser
                 20                  25                  30

Ser Tyr Lys Tyr Asp Cys Gly Asn Tyr Ala Gly Cys Cys Leu Pro Arg
             35                  40                  45

Asn Pro Tyr Gly Arg Val Lys Tyr Tyr Cys Thr Lys Lys Tyr Ser Cys
         50                  55                  60

Pro Asp Asp Phe Tyr Tyr Tyr Asn Asn Lys Gly Tyr Tyr Tyr Tyr Asn
 65                  70                  75                  80

Asp Lys Asp Tyr Phe Asn Cys Gly Ser Tyr Asn Gly Cys Cys Leu Arg
                 85                  90                  95

Ser Gly Tyr
```

<210> SEQ ID NO 13
<211> LENGTH: 194
<212> TYPE: PRT
<213> ORGANISM: Artificial Sequence
<220> FEATURE:
<223> OTHER INFORMATION: Synthetic polypeptide

<400> SEQUENCE: 13

```
Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ser Ser Glu Glu
50                  55                  60

Tyr Lys Gly Gly Tyr Tyr Pro Gly Asn Ala Tyr His Tyr His Ser Gly
65                  70                  75                  80

Gly Ser Tyr His Gly Ser Gly Tyr His Gly Gly Tyr Lys Gly Lys Tyr
                85                  90                  95

Tyr Gly Lys Ala Lys Lys Tyr Tyr Lys Tyr Lys Asn Ser Gly Lys
            100                 105                 110

Tyr Lys Tyr Leu Lys Lys Ala Arg Lys Tyr His Arg Lys Gly Tyr Lys
        115                 120                 125

Tyr Tyr Gly Gly Ser Ser Ala Lys Pro Ser Tyr Pro Pro Thr Tyr Lys
130                 135                 140

Ala Lys Pro Ser Tyr Pro Pro Thr Tyr Lys Ala Lys Pro Ser Tyr Pro
145                 150                 155                 160

Pro Thr Tyr Lys Ala Lys Pro Ser Tyr Pro Pro Thr Tyr Lys Ala Lys
            165                 170                 175

Pro Ser Tyr Pro Pro Thr Tyr Lys Ala Lys Pro Ser Tyr Pro Pro Thr
        180                 185                 190

Tyr Lys
```

<210> SEQ ID NO 14
<211> LENGTH: 196
<212> TYPE: PRT
<213> ORGANISM: Artificial Sequence
<220> FEATURE:
<223> OTHER INFORMATION: Synthetic polypeptide

<400> SEQUENCE: 14

```
Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ser Ser Glu Glu
50                  55                  60

Tyr Lys Gly Gly Tyr Tyr Pro Gly Asn Thr Tyr His Tyr His Ser Gly
65                  70                  75                  80

Gly Ser Tyr His Gly Ser Gly Tyr His Gly Gly Tyr Lys Gly Lys Tyr
                85                  90                  95

Tyr Gly Lys Ala Lys Lys Tyr Tyr Lys Tyr Lys Asn Ser Gly Lys
            100                 105                 110
```

```
Tyr Lys Tyr Leu Lys Lys Ala Arg Lys Tyr His Arg Lys Gly Tyr Lys
            115                 120                 125
Lys Tyr Tyr Gly Gly Ser Ser Ala Lys Pro Ser Tyr Pro Pro Thr
        130             135                 140
Tyr Lys Ala Lys Pro Ser Tyr Pro Pro Thr Tyr Lys Ala Lys Pro Ser
145                 150                 155                 160
Tyr Pro Pro Thr Tyr Lys Ala Lys Pro Ser Tyr Pro Pro Thr Tyr Lys
                165                 170                 175
Ala Lys Pro Ser Tyr Pro Pro Thr Tyr Lys Ala Lys Pro Ser Tyr Pro
            180                 185                 190
Pro Thr Tyr Lys
        195

<210> SEQ ID NO 15
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 15

Arg Gly Asp
1

<210> SEQ ID NO 16
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 16

Gly Arg Gly Asp Ser Pro
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 17

Pro His Ser Arg Asn Arg Gly Asp Ser Pro
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 18

Ser Pro Pro Arg Arg Ala Arg Val Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 19
```

```
Trp Gln Pro Pro Arg Ala Arg Ile
1               5

<210> SEQ ID NO 20
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 20

Lys Asn Asn Gln Lys Ser Glu Pro Leu Ile Gly Arg Lys Lys Thr
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 21

Arg Lys Arg Leu Gln Val Gln Leu Ser Ile Arg Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 22

Gly Lys Asn Thr Gly Asp His Phe Val Leu Tyr Met
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 23

Val Val Ser Leu Tyr Asn Phe Glu Gln Thr Phe Met Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 24

Arg Phe Asp Gln Glu Leu Arg Leu Val Ser Tyr Asn
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 25
```

```
Arg Leu Val Ser Tyr Ser Gly Val Leu Phe Leu Lys
1               5                   10
```

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 26

```
Ala Ser Lys Ala Ile Gln Val Phe Leu Leu Gly Gly
1               5                   10
```

<210> SEQ ID NO 27
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 27

```
Thr His Arg Pro Pro Met Trp Ser Pro Val Trp Pro
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 28

```
Thr Val Phe Ser Val Asp Gln Asp Asn Met Leu Glu
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 29

```
Arg Leu Arg Gly Pro Gln Arg Val Phe Asp Leu His
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 30

```
Phe Asp Leu His Gln Asn Met Gly Ser Val Asn
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 31

```
Gln Gln Asn Leu Gly Ser Val Asn Val Ser Thr Gly
```

<210> SEQ ID NO 32
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 32

Ser Arg Ala Thr Ala Gln Lys Val Ser Arg Arg Ser
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 33

Ala Asn Arg Tyr Leu Ala Met Lys Glu Asp Gly Arg Leu Leu Ala Ser
1               5                   10                  15

<210> SEQ ID NO 34
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 34

His Phe Lys Asp Pro Lys Arg Leu Tyr Cys Lys
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 35

Phe Leu Pro Met Ser Ala Lys Ser
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 36

Lys Thr Gly Pro Gly Gln Lys Ala
1               5

<210> SEQ ID NO 37
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 37

Leu Thr Gly Lys Asn Phe Pro Met Phe His Arg Asn
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 38

Met His Arg Met Pro Ser Phe Leu Pro Thr Thr Leu
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 39

Leu Cys Cys Gly Arg Gly His Arg Thr Arg Thr Gln Arg Val Thr Glu
1               5                   10                  15

Arg Cys Asn Cys
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 40

Leu Gly Thr Gln Gly Arg Leu Cys Asn Lys Thr Ser Glu Gly Met Asp
1               5                   10                  15

Gly Cys Glu Leu
            20

<210> SEQ ID NO 41
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 41

Ile Val Pro Leu Leu Leu Leu Val Leu His
1               5                   10

<210> SEQ ID NO 42
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 42

Tyr Thr Ala Gln Gly Glu Pro Phe Pro Asn Asn Val Glu Lys Leu Cys
1               5                   10                  15

Ala Pro

<210> SEQ ID NO 43
<211> LENGTH: 6
<212> TYPE: PRT
<213> ORGANISM: Artificial Sequence

```
<220> FEATURE:
<223> OTHER INFORMATION: Synthetic polypeptide

<400> SEQUENCE: 43

Lys Leu Asp Ala Pro Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 44

Glu Ile Leu Asp Val Pro Ser Thr Thr
1               5

<210> SEQ ID NO 45
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 45

Thr Trp Tyr Lys Ile Ala Phe Gln Arg Asn Arg Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 46

Asn Arg Trp His Ser Ile Tyr Ile Thr Arg Phe Gly
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Trp Tyr Val Ala Leu Lys Arg Thr Gly Gln Tyr Lys Leu Gly
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Arg Asn Ile Ala Glu Ile Lys Asp Ile
1               5

<210> SEQ ID NO 49
<211> LENGTH: 6
<212> TYPE: PRT
<213> ORGANISM: Artificial Sequence
<220> FEATURE:
```

```
<223> OTHER INFORMATION: Synthetic

<400> SEQUENCE: 49

Ala Asp Thr Pro Pro Val
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic

<400> SEQUENCE: 50

Gly Ile Ile Phe Phe Leu
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic

<400> SEQUENCE: 51

Arg Tyr Val Val Leu Pro Arg
1               5

<210> SEQ ID NO 52
<211> LENGTH: 16
<212> TYPE: PRT
<213> ORGANISM: Artificial Sequence
<220> FEATURE:
<223> OTHER INFORMATION: Synthetic

<400> SEQUENCE: 52

Lys Asn Asn Gln Lys Ser Glu Pro Leu Leu Ile Gly Arg Lys Lys Thr
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic

<400> SEQUENCE: 53

Lys Lys Gln Arg Phe Arg His Arg Asn Arg Lys Gly Tyr Arg Ser Gly
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Leu Phe Ser His Ala Val Ser Ser Asn Gly
1               5                   10

<210> SEQ ID NO 55
<211> LENGTH: 5
<212> TYPE: PRT
<213> ORGANISM: Artificial Sequence
<220> FEATURE:
<223> OTHER INFORMATION: Synthetic
```

```
<400> SEQUENCE: 55

Asp Gln Asn Asp Asn
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic

<400> SEQUENCE: 56

Leu Arg Ala His Ala Val Asp Ile Asn Gly
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic

<400> SEQUENCE: 57

Ala Thr Glu Thr Thr Ile Thr Ile Ser
1               5

<210> SEQ ID NO 58
<211> LENGTH: 19
<212> TYPE: PRT
<213> ORGANISM: Artificial Sequence
<220> FEATURE:
<223> OTHER INFORMATION: Synthetic

<400> SEQUENCE: 58

Tyr Glu Lys Pro Gly Ser Pro Pro Arg Glu Val Val Pro Arg Pro Arg
1               5                   10                  15

Pro Gly Val

<210> SEQ ID NO 59
<211> LENGTH: 6
<212> TYPE: PRT
<213> ORGANISM: Artificial Sequence
<220> FEATURE:
<223> OTHER INFORMATION: Synthetic

<400> SEQUENCE: 59

Gly Leu Pro Gly Glu Arg
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic

<400> SEQUENCE: 60

Ile Lys Val Ala Val
1               5

<210> SEQ ID NO 61
<211> LENGTH: 8
<212> TYPE: PRT
<213> ORGANISM: Artificial Sequence
<220> FEATURE:
```

```
<223> OTHER INFORMATION: Synthetic

<400> SEQUENCE: 61

Ser Pro Pro Arg Arg Ala Arg Val
1               5

<210> SEQ ID NO 62
<211> LENGTH: 4
<212> TYPE: PRT
<213> ORGANISM: Artificial Sequence
<220> FEATURE:
<223> OTHER INFORMATION: Synthetic

<400> SEQUENCE: 62

Arg Glu Asp Val
1

<210> SEQ ID NO 63
<211> LENGTH: 16
<212> TYPE: PRT
<213> ORGANISM: Artificial Sequence
<220> FEATURE:
<223> OTHER INFORMATION: Synthetic

<400> SEQUENCE: 63

Tyr Arg Val Arg Val Thr Pro Lys Glu Lys Thr Gly Pro Met Lys Glu
1               5                   10                  15

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Trp His Ser Ile Tyr Ile Thr Arg Phe Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Arg Asn Ile Ala Glu Ile Ile Lys Asp Ile
1               5                   10

<210> SEQ ID NO 66
<211> LENGTH: 16
<212> TYPE: PRT
<213> ORGANISM: Artificial Sequence
<220> FEATURE:
<223> OTHER INFORMATION: Synthetic

<400> SEQUENCE: 66

Lys Lys Gln Arg Phe Arg His Arg Asn Arg Lys Gly Tyr Arg Ser Gln
1               5                   10                  15

<210> SEQ ID NO 67
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 67

Gly Lys Asn Thr Gly Asp His Phe Val Leu Tyr Met
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Synthetic

<400> SEQUENCE: 68

Gly Phe Pro Gly Glu Arg
1               5

<210> SEQ ID NO 69
<211> LENGTH: 4
<212> TYPE: PRT
<213> ORGANISM: Artificial Sequence
<220> FEATURE:
<223> OTHER INFORMATION: Synthetic

<400> SEQUENCE: 69

Asp Gly Glu Ala
1

<210> SEQ ID NO 70
<211> LENGTH: 5
<212> TYPE: PRT
<213> ORGANISM: Artificial Sequence
<220> FEATURE:
<223> OTHER INFORMATION: Synthetic

<400> SEQUENCE: 70

Tyr Ile Gly Ser Arg
1               5

<210> SEQ ID NO 71
<211> LENGTH: 4
<212> TYPE: PRT
<213> ORGANISM: Artificial Sequence
<220> FEATURE:
<223> OTHER INFORMATION: Synthetic

<400> SEQUENCE: 71

Gly Glu Phe Tyr
1

<210> SEQ ID NO 72
<211> LENGTH: 5
<212> TYPE: PRT
<213> ORGANISM: Artificial Sequence
<220> FEATURE:
<223> OTHER INFORMATION: Synthetic

<400> SEQUENCE: 72

Pro His Ser Arg Asn
1               5
```

THREE-DIMENSIONAL MICRO-ENVIRONMENT STRUCTURE FOR CONTROLLING CELL BEHAVIOR, THREE-DIMENSIONAL SURFACE FOR CONTROLLING CELL BEHAVIOR, AND METHOD FOR MANUFACTURING ARRAY AND THREE-DIMENSIONAL MICRO-ENVIRONMENT STRUCTURE

RELATED APPLICATIONS

This application is a national stage filing under 35 U.S.C. § 371 of International Patent Application Serial No. PCT/KR2016/014319, filed Dec. 7, 2016, entitled "Three-Dimensional Micro-Environment Structure for Controlling Cell Behavior, Three-Dimensional Surface for Controlling Cell Behavior, and Method for Manufacturing Array and Three-Dimensional Micro-Environment Structure," which is incorporated herein by reference in its entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Feb. 2, 2023, is named A125370000US00-SUBSEQ-TC and is 22,591 bytes in size.

TECHNICAL FIELD

The present disclosure relates to a three-dimensional microenvironment structure for controlling the behavior of cells, including stem cells such as pluripotent stem cells, a surface and an array for controlling cell behavior, and a method for manufacturing the three-dimensional microenvironment structure.

BACKGROUND ART

The cellular microenvironment, defined by biochemical cues and physical cues, is a deciding factor in a wide range of cell behaviors, including cell adhesion, growth, differentiation, and expression of cell-specific functions. It is well known that cells generally interact with their surrounding microenvironment to survive and biologically function or to determine their direction of differentiation.

Most cells in tissues are surrounded on all sides by a complex set of extracellular matrix proteins that are critical in guiding cell function. Cells bind to the extracellular matrix via specific cell surface receptors such as integrin receptors, and this binding serves as a biochemical cue that can directly affect cell function. In addition, the extracellular matrix acts as a modulator of biochemical and mechanical stimuli that are present in tissues. For example, extracellular matrix proteins can sequester and release growth factors, control the rate of nutrient supply, as well as control the cell shape and transmit mechanical signals to the cell surface. The mechanical compliance of the extracellular matrix is also an important factor in controlling cell function. Thus, the ultimate fate of a cell to grow, differentiate, migrate, apoptose or perform other specific functions can be considered a coordinated response to the molecular interactions with these extracellular matrix microenvironmental effectors.

Many attempts have been made to create a three-dimensional microenvironment by incorporating cell adhesion ligands into biomaterials. Biologically derived or synthetic materials have been explored as an extracellular matrix microenvironment to gain control over the material and thus over the cellular behavior they induced. In one example, a crosslinkable hyaluronic acid, alginate or polyethylene glycol-based hydrogel having an RGD peptide motif was grafted onto a polymer backbone.

Complexities associated with native extracellular matrix proteins, including complex structural composition, purity, immunogenicity and pathogen transmission, have driven the development of synthetic biomaterials for use as two-dimensional or three-dimensional extracellular matrix microenvironment mimetics in order to mimic the regulatory characteristics of natural extracellular matrices and extracellular matrix-bound growth factors.

Extracellular matrix and growth factor signaling environments are important mechanisms for regulating cell fate. These microenvironmental stimuli are processed through combinatorial signaling pathways. Interactions between these signaling pathways are critical in determining cell fate. For example, fibroblast proliferation and differentiation into myofibroblasts, and increased collagen synthesis are key events in normal wound repair, and the fibroblast proliferation and differentiation are controlled by combinatorial signaling pathways (Non-Patent Document 1). However, conventional technologies do not create a microenvironment that induces combinatorial signaling pathways by simultaneously activating at least two different cell surface receptors, due to their lack of physical or biochemical cues. The present inventors have studied a technology capable of finely controlling cell behaviors, such as cell adhesion, migration, growth and differentiation, thereby completing the present disclosure.

SUMMARY OF DISCLOSURE

The present disclosure is directed to a three-dimensional microenvironment structure capable of accurately controlling cell behaviors, such as cell adhesion, migration, growth and differentiation, a surface and an array for controlling cellular behavior, and a method for manufacturing a three-dimensional microenvironment structure.

DISCLOSURE

Technical Problem

An object of the present disclosure is to provide a three-dimensional microenvironment structure capable of accurately controlling cell behaviors, such as cell adhesion, migration, growth and differentiation, a surface and an array for controlling cellular behavior, and a method for manufacturing a three-dimensional microenvironment structure.

Technical Solution

The present disclosure provides a three-dimensional microenvironment structure for controlling cell behavior comprising: a nanofiber membrane; and two or more peptide motifs, including a P1 (first peptide) motif and a P2 (second peptide) motif.

In the present disclosure, the two or more peptide motifs may bind to two or more different receptors on the cell, thereby generating a signal for controlling the cell behavior.

In the present disclosure, the cell behavior may be one or more selected from the group consisting of cell adhesion, migration, growth, proliferation, morphogenesis, differentiation and apoptosis.

In the present disclosure, the cell behavior may be cell growth.

In the present disclosure, the nanofiber membrane may comprise one or more of PVDF, PAN, PES, PU and PLA.

In the present disclosure, the P1 (first peptide) motif in the peptide motifs may control integrin receptor activity, and the P2 (second peptide) motif may control integrin coreceptor activity, thereby generating a signal for controlling the cell behavior.

In the present disclosure, the coreceptor may be one or more of FGF receptor, Frizzled receptor, TGF receptor, EGF receptor, LIF receptor, BMP receptor, cadherin, syndecan, and interleukin receptor.

In the present disclosure, the P1 (first peptide) motif may activate one or more of α3β1, α5β1, α6β1, α9β1, αvβ, αvβ5 integrin receptors and heparin receptors.

In the present disclosure, the P1 (first peptide) motif may activate α5β1 integrin receptor.

In the present disclosure, the P1 (first peptide) motif may be selected from RGD, PHSRN-RGDSP (SEQ ID NO: 17), GRGDSP (SEQ ID NO: 16), KLDAPT (SEQ ID NO: 43), SPPRRARVT (SEQ ID NO: 18), and KNNQKSEPLI-GRKKT (SEQ ID NO: 20).

In the present disclosure, the P1 (first peptide) motif may be PHSRN-RGDSP (SEQ ID NO: 17).

In the present disclosure, the P1 (first peptide) motif may activate α6β1 integrin receptor.

In the present disclosure, the P1 (first peptide) motif may be derived from the LG domain of laminin α5.

In the present disclosure, the P1 (first peptide) motif may be selected from GKNTGDHFVLYM (SEQ ID NO: 22), VVSLYNFEQTFML (SEQ ID NO: 23), RFDQELRLVSYN (SEQ ID NO: 24), RLVSYSGVLFFLK (SEQ ID NO: 25), ASKAIQVFLLGG (SEQ ID NO: 26), VLVRVERATVFS (SEQ ID NO: 27), TVFSVDQDNMLE (SEQ ID NO: 28), RLRGPQRVFDLH (SEQ ID NO: 29), FDLHQNMGSVN (SEQ ID NO: 30), QQNLGSVNVSTG (SEQ ID NO: 31), and SRATAQKVSRRS (SEQ ID NO: 32).

In the present disclosure, the P1 (first peptide) motif may be VVSLYNFEQTFML (SEQ ID NO: 23).

In the present disclosure, the P1 (first peptide) motif may activate each of integrin α5β1 and α6β1.

In the present disclosure, the P1 (first peptide) motif may be either PHSRN-RGDSP (SEQ ID NO: 17) as an integrin α5β1 activation motif or VVSLYNFEQTFML (SEQ ID NO: 23) as an integrin α5β1 activation motif.

In the present disclosure, the coreceptor may comprise Frizzled receptor, LIF receptor, FGF receptor and TGF receptor.

In the present disclosure, the coreceptor may be three coreceptors selected from Frizzled receptor, LIF receptor, FGF receptor and TGF receptor.

In the present disclosure, the coreceptor may be two coreceptors selected from Frizzled receptor, LIF receptor, FGF receptor and TGF receptor.

In the present disclosure, the coreceptor may be Frizzled receptor and TGF receptor.

In the present disclosure, the coreceptor may be Frizzled receptor.

In the present disclosure, the P1 (first peptide) motif in the peptide motifs may control TGF receptor activity, and the P1 (first peptide) motif may control TGF coreceptor activity.

In the present disclosure, the coreceptor may be one or more of Frizzled receptor, FGF receptor, EGF receptor, cadherin, syndecan, and interleukin receptor.

In the present disclosure, the coreceptor may be FGF receptor and Frizzled receptor.

In the present disclosure, the motif that activates Frizzled receptor may be one or more selected from LCCGRGHR-TRTQRVTERCNC (SEQ ID NO: 39) and LGTQGRLCNKTSEGMDGCEL (SEQ ID NO: 40).

In the present disclosure, the motif that activates TGF receptor may be selected from MHRMPSFLPTTL (SEQ ID NO: 38) or LTGKNFPMFHRN (SEQ ID NO: 37) L.

In the present disclosure, the motif that activates FGF receptor may be selected from FLPMSAKS (SEQ ID NO: 35), HFKDPKRLYCK (SEQ ID NO: 34), ANRYLAM-KEDGRLLAS (SEQ ID NO: 33), KTGPGQKA (SEQ ID NO: 36), or WYVALKRTGQYKLG (SEQ ID NO: 47).

In the present disclosure, the P2 (second peptide) motif may be a motif that activates LIF receptor, and may be selected from IVPLLLLVLH (SEQ ID NO: 41), and YTAQGEPFPNNVEKLCAP (SEQ ID NO: 42).

In the present disclosure, the peptide motifs may be introduced at a concentration of 0.001 mg/ml to 10 mg/ml.

In the present disclosure, the peptide motifs may be those attached to an adhesive protein.

In the present disclosure, the adhesive protein may be a mussel adhesive protein.

The present disclosure provides a surface for controlling cell behavior, the surface comprising two or more peptide motifs, including a P1 (first peptide) motif and a P2 (second peptide) motif, which bind to cell receptors, wherein the peptide motifs bind to two or more different receptors on the cell, thereby generating a signal for controlling the cell behavior.

The surface may be a porous surface, a non-porous surface, or a combination thereof.

The surface may be the surface of one or more of a nanofiber, a hydrogel and a particle.

In the present disclosure, the cell behavior may be one or more selected from the group consisting of cell adhesion, migration, growth, proliferation, morphogenesis, differentiation or apoptosis.

In the present disclosure, the two or more different receptors may be integrin receptor and integrin coreceptor.

In the present disclosure, the coreceptor may be one or more selected from among FGF receptor, Frizzled receptor, TGF receptor, EGF receptor, LIF receptor, BMP receptor, cadherin, syndecan, and interleukin receptor.

In the present disclosure, the coreceptor may be one or more of FGF receptor, Frizzled receptor, TGF receptor, EGF receptor, LIF receptor, BMP receptor, cadherin, syndecan, and interleukin receptor.

In the present disclosure, the coreceptor may be one or more selected from among FGF receptor, BMP receptor, EGF receptor, and Frizzled receptor.

In the present disclosure, the coreceptor may be Frizzled receptor.

In the present disclosure, the coreceptor may be FGF receptor.

In the present disclosure, the two or more different receptors may be any one of integrin-Frizzled receptor, integrin-LIF receptor, integrin-BMP receptor, integrin-FGF receptor, and integrin-EGF receptor.

In the present disclosure, the two or more peptide motifs may be an integrin-binding motif and an integrin coreceptor-binding motif.

In the present disclosure, the integrin-binding motif may bind to one or more of a3b1, a5b1, a6b1, a9b1 and avb3 integrins.

In the present disclosure, the integrin coreceptor-binding motif may be a motif that binds to one or more of integrin- Frizzled receptor, integrin-LIF receptor, integrin-BMP receptor, integrin-FGF receptor, and integrin-EGF receptor.

In the present disclosure, the two or more peptide motif may be PHSRN-RGDSP (SEQ ID NO: 17).

The present disclosure provides an array for controlling cell behavior, the array comprising two or more selected from the above structure and the above surface.

The present disclosure provides a method for manufacturing a three-dimensional microenvironment structure for controlling cell behavior, the method comprising the steps of: 1) preparing a composition containing one or more polymer materials selected from among PVDF, PAN, PES and PLA; 2) preparing a composition containing peptide motifs; and 3) mixing the composition of 1) and the composition of 2), followed by electrospinning.

The present disclosure provides a method for manufacturing a three-dimensional microenvironment structure for controlling cell behavior, the method comprising the steps of: 1) electrospinning a composition containing one or more polymer materials selected from among PVDF, PAN, PES and PLA, thereby manufacturing a three-dimensional structure; and 2) coating the three-dimensional structure with a composition containing peptide motifs.

Advantageous Effects

The three-dimensional microenvironment structure, surface, array and three-dimensional microenvironment structure manufacturing method of the present disclosure have the effect of accurately controlling cell behaviors, such as cell adhesion, migration, growth and differentiation.

DESCRIPTION OF DRAWINGS

FIG. 1 shows the results of silver staining performed to confirm that a peptide motif functioning as an extracellular matrix mimetic is located on the nanofiber surface.

FIG. 2A depicts photographs of nanofibers having fiber diameters of 200 nm, 500 nm and 800 nm, respectively, and FIG. 2B depicts photographs of nanofibers having fiber diameters of 600 nm and 1000 nm, respectively.

FIG. 3 shows results indicating that when an extracellular matrix mimetic is introduced to the nanofiber surface, particles having a particle size of 500 nm to 5 μm can be obtained.

FIG. 4 is an example of an array layout of the present disclosure. Circle A2 shows SEQ ID NO: 17. Circle A3 shows SEQ ID NO: 61. Circle A4 shows SEQ ID NO: 19. Row B shows SEQ ID NOs: 62, 43, 63, and 57 from left to right, respectively. Row C shows SEQ ID NOs: 58 and 20 from left to right, respectively.

FIG. 5 schematically represents membranes having a peptide motif located on the surface thereof.

FIG. 6A is an example of a structure of the present disclosure. SEQ ID NOs: 40, 33, 17, and 64 are shown from left to right, respectively.

FIG. 6B shows the results of fluorescent staining performed to confirm that a peptide motif is present on the nanofiber membrane surface.

FIG. 6C shows the effects of protein blending and spinning and a motif on the adhesion of cells (mESCs).

FIG. 7 shows an array for coating and evaluating 20 peptides according to the present disclosure. Circle A4 shows SEQ ID NO: 17. Row B shows SEQ ID NOs: 18, 45, 21, and 46 from left to right, respectively. Row C shows SEQ ID NOs: 39, 40, 41 and 42 from left to right, respectively.

FIG. 8 shows results indicating that peptides derived from fibronectin (such as PHSRN-RGDSP (SEQ ID NO: 17)), laminin (such as RNIAEIKDI (SEQ ID NO: 48)) or cadherin (such as ADTPPV (SEQ ID NO: 49)) are effective for stem cell adhesion and colony formation. The second row shows SEQ ID NOs: 15, 17, 18, 45, and 21 from left to right, respectively. The bottom row shows SEQ ID NOs: 46, 39, 40, 41, and 42 from left to right, respectively.

FIG. 9 shows results indicating that peptides derived from fibronectin (such as PHSRN-RGDSP (SEQ ID NO: 17)), laminin (such as RNIAEIKDI (SEQ ID NO: 48)) or cadherin (such as ADTPPV (SEQ ID NO: 49)) are effective for stem cell adhesion and colony formation. SEQ ID NOs: 50, 51, and 65 ae shown from left to right in the second row. SEQ ID NOs: 19, 20, and 66 are shown from left to right in the third row.

FIG. 10A shows results indicating that peptides derived from fibronectin (such as PHSRN-RGDSP (SEQ ID NO: 17)), laminin (such as RNIAEIKDI (SEQ ID NO: 48)) or cadherin (such as ADTPPV (SEQ ID NO: 49)) are effective for stem cell adhesion and colony formation. The second row shows SEQ ID NOs: 54, 49, 55, and 56 from left to right, respectively.

FIG. 10B shows results indicating that peptides derived from fibronectin (such as PHSRN-RGDSP (SEQ ID NO: 17)), laminin (such as RNIAEIKDI (SEQ ID NO: 48)) or cadherin (such as ADTPPV (SEQ ID NO: 49)) are effective for stem cell adhesion and colony formation. The last box in the first row shows SEQ ID NO: 67. The second row shows SEQ ID NOs: 23-27 from left to right, respectively. The third row shows SEQ ID NOs: 28-32 from left to right, respectively.

FIG. 11 shows the results of AP staining performed to examine the effects of each motif on embryonic stem cell self-renewal and colony size. SEQ ID NO: 17 is shown in the third column.

FIG. 12 shows the effect of a coating method (2D plate coating) used for protein coating.

FIG. 13 shows the results of AP staining performed to examine the effects of simultaneous control of activities of two key receptors on embryonic stem cell self-renewal and colony size.

FIG. 14A shows the results of AP staining performed to examine the effects of simultaneous control of activities of two key receptors on embryonic stem cell self-renewal and colony size.

FIG. 14B shows the results of AP staining performed to examine the effects of simultaneous control of activities of two key receptors on embryonic stem cell self-renewal and colony size.

FIG. 15 shows the results of two-dimensionally examining the effects of protein motifs in hiPSCs.

FIG. 16 shows the results of two-dimensionally examining the effects of protein motifs in hiPSCs.

FIG. 17 shows the results of AP staining.

FIG. 18 shows the results of examining the effect of the density of a PHSRN-RGDSP (SEQ ID NO: 17) motif in mESCs.

FIG. 19 shows the effect of protein coating concentration on hiPSC culture (2D plate).

FIG. 20 shows the results of controlling the thicknesses of PVDF membranes.

FIG. 21 shows a microenvironment array comprising individual motifs alone. SEQ ID NO: 60 is shown in circles A1-A3. SEQ ID NO: 59 is shown in circles A4-A6. SEQ ID NO: 68 is shown in circles B4-B6. SEQ ID NO: 69 is shown in circles C4-C6. SEQ ID NO: 70 is shown in circles D1-D3, and SEQ ID NO: 71 is shown in circles D4-D6.

FIG. 22 is a graph showing the effect of each peptide motif on the migration of cells. SEQ ID NOs: 69, 71, 68, 59, 60, and 70 are shown on the X-axis from left to right, respectively.

FIG. 23A shows the representative results of a scratch test.

FIG. 23B shows the representative results of a scratch test. The motif IKVAV (SEQ ID NO: 60) is shown on the left-hand side.

FIG. 24 shows the results of an experiment performed in Example 12 of the present disclosure.

FIG. 1

Mode for Invention

The present disclosure is directed to a three-dimensional microenvironment structure capable of accurately controlling cell behaviors, such as cell adhesion, migration, growth and differentiation, a surface and an array for controlling cell behavior, and a method for manufacturing the three-dimensional microenvironment structure.

The "three-dimensional structure" in the present disclosure is meant to include any three-dimensional structure which is used for the purpose of cell adhesion, migration, growth and differentiation. In addition, the "microenvironment" in the present disclosure is any biological, chemical and physical element for realizing a natural extracellular matrix outside cells.

The three-dimensional microenvironment structure for controlling cell behavior according to the present disclosure comprises a nanofiber membrane and peptide motifs.

The present disclosure provides a three-dimensional microenvironment structure for controlling cell behavior including: a nanofiber membrane; and two or more peptide motifs, including a P1 (first peptide) motif and a P2 (second peptide) motif.

In the present disclosure, the cell behavior may be one or more selected from the group consisting of cell adhesion, migration, growth and differentiation. In particular, it is preferably cell growth.

The nanofiber membrane of the present disclosure may comprise nanofibers comprising or made of a polymer material. The polymer material may be a polymer which may be electrospun, and examples thereof include, but are not limited to, polyvinylidene (PVDF), polyacrylonitrile (PAN), polyethersulfone (PES), polylactic acid (PLA), polyglycolic acid (PGA), polylactide glycolic acid (PLGA), polycaprolactone, polyalkylene oxide, and the like. In particular, the nanofiber membrane of the present disclosure preferably comprises one or more of PVDF, PAN, PES and PLA.

The polymer material of the present disclosure may be selected from those having a molecular weight in the range of at least 100,000 to several million Daltons (Da), and preferably has a molecular weight of 300000 to 500000 Da.

The peptide motifs of the present disclosure may bind to receptors on the cells, thereby generating a signal for controlling the cell behavior. The two or more peptide motifs may be preferably included simultaneously, and thus may bind to two or more different receptors on the cells, thereby generating a signal for controlling the cell behavior.

In the present disclosure, the P1 (first peptide) motif in the peptide motifs may control integrin receptor activity, and the P2 (second peptide) motif may control integrin coreceptor activity, thereby generating a signal for controlling the cell behavior.

The peptide motifs of the present disclosure preferably include an integrin-binding motif and an integrin coreceptor-binding motif. The integrin-binding motif may be a motif that binds to one or more integrins selected from among a3b1, a5b1, a6b1, a9b1 and avb3 integrins, and the integrin coreceptor-binding motif may be a motif that binds to one or more receptors selected from among integrin-Frizzled receptor, integrin-LIF receptor, integrin-BMP receptor, integrin-FGF receptor, and integrin-EGF receptor.

Specifically, the peptide motifs of the present disclosure may control the activity of one or more of integrin-Frizzled receptor, integrin-LIF receptor, integrin-BMP receptor, integrin-FGF receptor, and integrin-EGF receptor.

In particular, in the present disclosure, an experiment on culture of human induced pluripotent stem cells, performed using two different receptors, revealed that the self-renewal and growth/proliferation effects were better in the order of cell receptor integrin-Frizzed receptor>integrin-LIF receptor>integrin-FGF receptor, and an experiment on culture of human induced pluripotent stem cells, performed using four different receptors in order to examine the effect of combinations on cell receptor activation, revealed that four types of combinations comprising Frizzled or TGFβ receptor had an excellent effect of maintaining colony size, self-renewal ability and differentiation ability.

The peptide motifs of the present disclosure preferably include one or more of RGD, PHSRN-RGDSP (SEQ ID NO: 17), SPPRRARVT (SEQ ID NO: 18), TWYKIAF (SEQ ID NO: 45), RKRLQVQLSIRT (SEQ ID NO: 21), NRWHSIYITRFG (SEQ ID NO: 46), GIIFFL (SEQ ID NO: 50), RYVVLPR (SEQ ID NO: 51), RNIAEIKDI (SEQ ID NO: 48), WQPPRARI (SEQ ID NO: 19), KNNQKSEPL-LIGRKKT (SEQ ID NO: 52), KKQRFRHRNRKGYRSG (SEQ ID NO: 53), LCCGRGHRTRTQRVTERCNC (SEQ ID NO: 39), LGTQGRLCNKTSEGMDGCEL (SEQ ID NO: 40), IVPLLLLVLH (SEQ ID NO: 41), YTAQGEPFPNNVEKLCAP (SEQ ID NO: 42), LFSHAVSSNG (SEQ ID NO: 54), ADTPPV (SEQ ID NO: 49), DQNDN (SEQ ID NO: 55), and LRAHAVDING (SEQ ID NO: 56), and preferably essentially include PHSRN-RGDSP (SEQ ID NO: 17).

The peptide motifs are preferably introduced to the three-dimensional microenvironment structure or the surface thereof at a concentration of 0.001 mg/ml to 10 mg/ml, most preferably 0.01 mg/ml to 1 mg/ml.

More preferably, the peptide motifs of the present disclosure may be those attached to a mussel adhesive protein. The mussel adhesive protein may be a commercially available material or may be synthesized or obtained from a natural source. Examples of commercially available mussel adhesive proteins include, but are not limited to, MAPTrix™ ECM marketed by Kollodis BioSciences, Inc. (North Augusta, South Carolina, USA). The MAPTrix™ ECM is a mussel adhesive protein-based extracellular matrix mimetic material developed by Kollodis BioSciences, Inc. This material is a mussel adhesive protein recombinantly functionalized with a variety of extracellular matrix-derived peptides in order to mimic the bioactivity of naturally occurring extracellular matrices, and was experimentally demonstrated to have a bioactivity similar to natural extracellular matrix proteins in primary cell cultures as compared to natural or recombinant extracellular matrix proteins. The pre-designed extracellular matrix mimetic MAPTrix™ ECM is highly advantageous for creating a synthetic three-dimensional extracellular matrix microenvironment structure. For example, it may provide a synthetic three-dimensional microenvironment structure which is regulated cell-specifically or depending on the user's definition, and thus it may precisely mimic the natural microenvironment so that the biochemical cues provided thereby will be similar to biological cues provided by the natural microenvironment.

The MAPTrix™ ECM is a mussel adhesive protein recombinantly functionalized with bioactive peptides. In the present disclosure, the mussel adhesive protein may be used either alone or as a fusion protein comprising: a first peptide corresponding to the C-terminus, N-terminus, or both, of foot protein FP-5 represented by any one of SEQ ID NOs: 8 to 10 or foot protein 3 (FP-3) represented by SEQ ID NO: 5 or 6; and at least one second peptide selected from the group consisting of the mussel adhesive protein FP-1 (SEQ ID NO: 1, 2 or 3) or fragments of each protein.

In the present disclosure, bioactive peptides are necessary to mimic the microenvironment structure of a natural extracellular matrix. Furthermore, additional components, such as growth factors, for example, fibroblast growth factor (FGF) or substance P, may also be included to further enhance the beneficial effect of the extracellular matrix mimetic material on cell and tissue culture, medical devices and treatments, or other related applications.

The bioactive peptides may be added to the C-terminus, N-terminus, or both, of the mussel adhesive protein by gene recombination technology. In addition, these bioactive peptides may be added not only to the C-terminus or N-terminus of the fused mussel adhesive protein, but also between the components of the fusion protein. For example, extracellular matrix- or growth factor-derived peptides may be added between the FP-1 and FP-5 of the fusion protein FP-151. Additionally, the bioactive peptides may be different extracellular matrix- or growth factor-derived peptides present at both ends or between the components of the fusion protein.

Bioactive peptides are natural or synthetic peptides derived from extracellular matrix proteins, and mimic the biochemical or biophysical cues of a natural extracellular matrix. The extracellular matrix proteins can be fibrous proteins, such as collagen, fibronectin, laminin, or vitronectin. The extracellular matrix proteins may influence the activity of cell surface receptors such as integrins, which may, in turn, bind to polyvalent extracellular matrix proteins, and then activate signaling pathways by co-clustering with kinases and adaptor proteins in focal adhesion complexes. For example, a RGD-containing peptide segment derived from fibronectin, laminin or vitronectin may regulate integrin activity.

The present disclosure provides a surface for controlling cell behavior, which may be a microenvironmentally defined 3D surface, a microenvironment surface or a three-dimensional microenvironment surface. The surface of the present disclosure is a surface for controlling cell behavior comprising two or more peptide motifs, including a P1 (first peptide) motif and a P2 (second peptide) motif, which bind to cell receptors, wherein the peptide motifs may bind to two or more different receptors on the cell, thereby generating a signal for controlling the cell behavior.

The surface of the present disclosure may mean a cell culture structure itself, such as a nanofiber, a hydrogel, a particle, cellulose, or a glass fiber, or may be the surface thereof. In particular, the surface may be a pattern or porous nanofiber itself composed of various materials, including polyvinylidene (PVDF), or may be the surface thereof.

The surface of the present disclosure may be a surface for controlling cell behavior comprising two or more peptide motifs which bind to cell receptors, wherein the peptide motifs may bind to two or more different receptors on the cell, thereby generating a signal for controlling the cell behavior.

In the present disclosure, the cell behavior may be one or more selected from the group consisting of cell adhesion, migration, growth and differentiation, and the two or more different receptors may be integrin receptor and integrin coreceptor. In addition, the two or more different receptors may be any one of integrin-Frizzled receptor, integrin-LIF receptor, integrin-BMP receptor, integrin-FGF receptor, and integrin-EGF receptor.

Meanwhile, the contents described above with respect to the three-dimensional microenvironment structure for controlling cell behavior are equally applied to all matters including the peptide motifs and/or receptors in the surface of the present disclosure.

In one example of the present disclosure, the surface comprises a substrate protein containing either a heparin-binding motif derived from fibronectin domain III or an α5β1 integrin-activating motif. The heparin-binding motif or the α5β1 integrin-activating motif is preferably selected from among RGD (SEQ ID NO: 15), GRGDSP (SEQ ID NO: 16), PHSRN-RGDSP (SEQ ID NO: 17), SPPRRARVT (SEQ ID NO: 18), WQPPRARI (SEQ ID NO: 19), KNNQKSEPLIGRKKT (SEQ ID NO: 20), or a combination of the α5β1 integrin that activates the motifs and the motif-bound heparin.

In another example, the surface of the present disclosure comprises a substrate protein containing an α6β1 integrin-activating motif derived from the laminin α5 LG domain or laminin α1, which supports stem cell self-renewal and pluripotency. The α6β1 integrin-activating motif is preferably selected from among GKNTGDHFVLYM (SEQ ID NO: 22), VVSLYNFEQTFML (SEQ ID NO: 23), RFDQELRLVSYN (SEQ ID NO: 24), RLVSYSGVLFFLK (SEQ ID NO: 25), ASKAIQVFLLGG (SEQ ID NO: 26), VLVRVERATVFS (SEQ ID NO: 27), TVFSVDQDNMLE (SEQ ID NO: 28), RLRGPQRVFDLH (SEQ ID NO: 29), FDLHQNMGSVN (SEQ ID NO: 30), QQNLGSVNVSTG (SEQ ID NO: 31), SRATAQKVSRRS (SEQ ID NO: 32), TWYKIAFQRNRK (SEQ ID NO: 45), and NRWHSIYITRFG (SEQ ID NO: 46).

In another example, the surface of the present disclosure comprises a substrate protein containing a combinatorial motif of an α6β1-binding motif and an α5β1 integrin-activating motif in order to support stem cell pluripotency and self-renewal. The combinatorial motif is preferably a combination of PHSRN-RGDSP (SEQ ID NO: 17) and NRWHSIYITRFG (SEQ ID NO: 46), which supports stem cell pluripotency and self-renewal.

The present disclosure provides an FGF mimetic comprising a recombinant mussel adhesive protein functionalized with an FGF-derived peptide motif derived from a canofin domain or a hexafin domain. The FGF mimetic peptide motif is preferably selected from among a canofin domain derived from HFKDPKRLYCK (SEQ ID NO: 34), FLPMSAKS (SEQ ID NO: 35) or KTGPGQKAIL (SEQ ID NO: 36), or a hexafin domain derived from ANRYLAMKEDGRLLAS (SEQ ID NO: 33).

The present disclosure provides an array for controlling cell behavior comprising two or more selected from the three-dimensional microenvironment structure and the surface.

One embodiment of the array for controlling cell behavior according to the present disclosure is shown in Example 4 and FIG. 7.

The contents described above with respect to the three-dimensional microenvironment structure for controlling cell behavior and/or the surface are equally applied to all matters including the peptide motifs and/or receptors in the array of the present disclosure.

The present disclosure provides a method for manufacturing a three-dimensional microenvironment structure for controlling cell behavior. Specifically, the method may comprise the steps of: 1) preparing a composition containing one or more polymer materials selected from among PVDF, PAN, PES and PLA; 2) preparing a composition containing peptide motifs; and 3) mixing the composition of 1) and the composition of 2), followed by electrospinning.

In addition, the method for manufacturing a three-dimensional microenvironment structure for controlling cell behavior according to the present disclosure may comprise the steps of: 1) electrospinning a composition containing one or more polymer materials selected from among PVDF, PAN, PES and PLA, thereby manufacturing a three-dimensional structure; and 2) coating the three-dimensional structure with a composition containing peptide motifs.

The contents described above with respect to the three-dimensional microenvironment structure for controlling cell behavior and/or the surface and/or the array are equally applied to all matters including the peptide motifs and/or receptors in the method for manufacturing a three-dimensional microenvironment structure for controlling cell behavior according to the present disclosure.

Hereinafter, the present disclosure will be described in more detail with reference to examples. However, these examples are only illustrative of the present disclosure, and the scope of the present disclosure is not limited thereto.

Example 1: Introduction of Peptide Motifs to Nanofiber Surface by Electrospinning Experimental Method
1) Preparation of Electrospinning Solution: Each of four synthetic polymers, PVDF (average molecular weight: 200 kDa; purchased from Sigma Aldrich (St. Louis, USA)), PAN (average molecular weight: 200 kDa), PES, and PLA (average molecular weight: 200 kDa; purchased from Sigma Aldrich (St. Louis, USA)), was prepared at a concentration of 12 to 18 wt % in the solvent DMAc.

2) Next, the extracellular matrix mimetic MAPTrix™ (purchased from Kollodis Biosciences (North Augusta, SC, USA)) was dissolved in a mixed solvent of water/DMAc, and then the synthetic polymer solutions of 1) were added thereto, thereby preparing electrospinning solutions having concentrations of 15 wt % and 18 wt %.

At this time, DMAc and THF were used as solvents, and the mixing ratio of the solvents was controlled to adjust the fiber diameter.

For example, in order to manufacture fibers having a fiber diameter of 200 nm, the concentration of the spinning solution was set at 15 wt % and the mixing ratio of the solvents (DMAc/THF) was set at 7/3. In this state, electrospinning was performed.

In order to manufacture fibers having a fiber diameter of 5,600 nm, the concentration of the spinning solution was set at 18 wt % and the mixing ratio of the solvents (DMAc/THF) was set at 7/3. In this state, electrospinning was performed.

In addition, in order to manufacture fibers having a fiber diameter of 800 to 1000 nm, the concentration of the spinning solution was set at 18 wt % and the mixing ratio of the solvents (DMAc/THF) was set at 5/5. In this state, electrospinning was performed.

As electrospinning conditions, a voltage of 21 kV and an injection rate of 0.1 mL/min were used, which were constant for all the spinning solutions, but the distance between the nozzle and the collector was adjusted to 10 to 11 cm so that nanofibers would be easily formed from each solution. While the temperature and humidity in a chamber were maintained at constant temperature and humidity (30° C. and 60%), electrospinning was performed. To control the fiber diameter, the temperature and the humidity were adjusted depending on spinnability and the fiber diameter distribution.

The composition and electrospinning conditions of each electrospinning are shown in Tables 1 and 2 below.

TABLE 1

Composition (structural components) of electrospunable solution

| Polymer | Solution | MAPTrix ™ | Solution (1 mL) |
|---|---|---|---|
| 100 mg PVDF | 5 mL DMAc | 7 mg | DW/DMAc (0.1/0.9) |
| 100 mg PES | 5 mL DMAc | 7 mg | DW/DMAc (0.1/0.9) |
| 100 mg PAN | 5 mL DMAc | 7 mg | DW/DMAc (0.1/0.9) |
| 100 mg PLGA | 5 mL DMAc | 7 mg | DW/DMAc (0.1/0.9) |
| 50 mg PVDF/ 50 mg PAN | 5 mL DMAc | 7 mg | DW/DMAc (0.1/0.9) |
| 50 mg PVDF/ 50 mg PES | 5 mL DMAc | 7 mg | DW/DMAc (0.1/0.9) |

TABLE 2

Parameters for Electrospinning

| E-solution | Concentration | Voltage (kV) | Rate (mL/min) | Distance (cm) |
|---|---|---|---|---|
| PVDF | 18% | 21 | 0.1 | 11 |
| PES | 18% | 21 | 0.1 | 10 |
| PAN | 18% | 21 | 0.1 | 10 |
| PLGA | 18% | 21 | 0.1 | 11 |
| PVDF/PAN | 18% | 21 | 0.1 | 10 |
| PVDF/PES | 18% | 21 | 0.1 | 10 |

The E-solution is an electrospunable bio-functional component prepared according to the above-described method.

Experimental Results

It was confirmed by an electron microscope that a nanofiber membrane was formed in which the peptide motif functioning as an extracellular matrix mimetic was located on the nanofiber surface. In addition, it was confirmed by a staining test that the peptide motif was present on the nanofiber surface. Namely, pure PVDF (PVDF control) was not stained, and thus did not change color, because the amine group ($-NH_2$) of the protein was not present thereon; however, the nanofiber surface having each protein (MAP, Combo, or RGD) added thereto could be stained due to the presence of the $NH_2$ group.

The experimental results are shown in FIG. 1. FIG. 1 shows the results of silver staining performed to confirm that a peptide motif functioning as an extracellular matrix mimetic is located on the nanofiber surface.

Functionalization to introduce a peptide motif onto the nanofiber surface according to a conventional art requires additional processes such as a surface treatment process of chemically immobilizing the peptide motif to introduce the peptide motif onto the nanofiber surface, but the present disclosure is based on the thermodynamic principle, and does not require the addition or supplementation of a conventional electrospinning process, indicating that the present disclosure has the advantages of being economical and simple.

Example 2: Nanofiber Membranes Having Controlled Fiber Diameters

Experimental Method

1) To control the nanofiber diameter, PVDF was selected as a representative, and PVDF copolymers miscible with the PVDF were used to prepare mixtures. As the PVDF copolymers, PVDF copolymers having molecular weights of 400,000, 600,000 and 650,000 were used to manufacture nanofiber membranes having various fiber diameters.

2) While the mixing ratio of the PVDF and the PVDF copolymer was changed from 1:1 to 1:2, 1:3, 1:4, 1:5, 1:6, 1:7, 1:8 and 1:9, the effect of the molecular weight and mixing ratio of the PVDF copolymer on the control of the diameter was observed.

The electrospinning procedure and conditions are the same as described in Example 1.

Experimental Results

The experimental results are shown in FIG. 2. FIG. 2A depicts photographs of nanofibers having fiber diameters of 200 nm, 500 nm and 800 nm, respectively, and FIG. 2B depicts photographs of nanofibers having fiber diameters of 600 nm and 1000 nm, respectively.

The experimental results revealed that optimization of the mixing ratio of the PVDF and the PVDF copolymer and the molecular weight of the PVDF made it possible to manufacture nanofiber membranes having fiber diameters of 200 nm, 500 nm and 800 nm, respectively.

The diameter of nanofibers is one of the important factors that affect cell adhesion and growth. In the present disclosure, a membrane substrate having a changed nanofiber diameter was achieved while a biochemical environment formed by an extracellular matrix was maintained constant. In a chemical immobilization method according to a conventional art, a constant density or orientation is not always realized, since the chemical reaction between the peptide motif and the nanofiber surface is a random reaction, but in the present disclosure, a membrane having a precisely controlled nanofiber diameter can be manufactured while a constant density or orientation is always maintained.

Example 3: Manufacture of Nanofibers Containing Particles

Experimental Method

1) To introduce particles composed of an extracellular matrix mimetic onto the surface of nanofibers, sodium bicarbonate was dissolved in 1 mL of water to obtain 10 mM buffer solution (pH 6.5), and 10 mg of EDC (1-ethyl-3-[3-dimethylaminopropyl]carbodiimide hydrochloride) and 5 mg of S-NHS were dissolved in the buffer solution, thereby preparing an aqueous solution.

2) Next, 0.1 mg of a mussel protein with the fibronectin mimetic PHSRN-RGDSP (SEQ ID NO: 17) peptide motif was dissolved in 1 mL of water, thereby preparing a reaction solution.

3) The EDC/S-NHS solution was added to a nanofiber membrane-coated micro well plate and incubated for 30 minutes so that the —COOH group of MAPTrix present on the nanofiber membrane surface was activated.

Thereafter, the reaction solution of 2) was added to the nanofiber surface so that it reacted with the —COOH group on the nanofiber surface to form particles.

Experimental Results

The experimental results are shown in FIG. 3. FIG. 3 shows results indicating that when an extracellular matrix mimetic is introduced to the nanofiber surface, particles having a particle size of 500 nm to 5 m can be obtained.

The surface topography of the nanofibers is one of the important factors constituting a cellular microenvironment, and it was confirmed that a peptide motif was present on the particle surface, making it possible to manufacture a membrane capable of more precisely controlling cell behavior by a combination of the surface topography and the peptide motif.

Example 4: Preparation of Microenvironment Array

Example 4-1: Attachment of Peptide Motif to Nanofiber Membrane Surface

Experimental Method

1) Nanofiber membranes having each of 12 fibronectin-derived peptide motifs present on the surface thereof were prepared according to Example 1 (see the layout shown in FIG. 4).

2) Next, the membrane comprising each peptide motif was coated on a 12-well plate, and FIG. 4 shows an array layout.

3) At this time, the sequences of 10 peptide motifs, including the sequences of SEQ ID NOs: 15 to 20 and 43, are described as representatives in the specification.

Experimental Results

FIG. 5 depicts electron micrographs of membranes having fiber diameters of 200 nm, 500 nm and 800 nm, respectively. FIG. 5 schematically represents membranes having a peptide motif located on the surface thereof, and FIG. 6B shows the results of fluorescent staining performed to confirm that a peptide motif is present on the nanofiber membrane surface.

From the experimental results, it was confirmed that the peptide motif was present on the nanofiber surface and membranes having fiber diameters of 200 nm, 500 nm and 800 nm could be manufactured, making it possible to manufacture a cell culture surface capable of precisely controlling a cellular microenvironment.

In addition, FIG. 6C shows the effects of protein blending and spinning and a motif on the adhesion of cells (mESCs), and the terms used therein indicate the following:

PVDF: a sample obtained by spinning only PVDF;

PVDF-MAP: a sample obtained by blending and spinning MAP (mussel adhesive protein) during spinning of PVDF;

PVDF-Combo: a sample obtained by blending and spinning Combo (MAP-Combo (fibronectin motif: PHSRN (SEQ ID NO: 72)+GRGDSP (SEQ ID NO: 16))) during spinning of PVDF.

From the experimental results, it was confirmed that when only PVDF was spun, mESCs hardly adhered, but when the protein was blended and spun with PVDF, a large amount of the cells adhered, and when the motif (Combo) was used, a larger amount of the cells adhered. In addition, the adhesion of the cells was higher in the order of PVDF<PVDF-MAP<PVDF-Combo. Additionally, blending and spinning of the protein was effective and made the motif effective.

Example 4-2: Selection of Peptide Motif Effective for Stem Cell Adhesion and Colony Formation Experimental Method 1) The 600-nm nanofiber membrane manufactured by blending and spinning Combo according to Example 1 was coated with each of 20 peptides, including fibronectin, laminin, WNT, LIF, and cadherin-like peptide, thereby preparing an array (FIG. 7 shows an array for coating and evaluating 20 types of peptides according to the present disclosure).

2) In order to realize various microenvironments using peptides alone or in combination, MAPTrix™ comprising an integrin-binding motif, such as RGD (SEQ ID NO: 15), GRGDSP (SEQ ID NO: 16), PHSRN-RGDSP (SEQ ID NO: 17) or KLDAPT (SEQ ID NO: 43), which binds to integrin, LIF or Frizzled receptor, and a heparin-binding motif, such as SPPRRARVT (SEQ ID NO: 18), WQPPRARI (SEQ ID NO: 19), KNNQKSEPLIGRKKT (SEQ ID NO: 20), ATETTITIS (SEQ ID NO: 57), or YEKPGSPPREVVPRPRPGV (SEQ ID NO: 58), was used to create an extracellular microenvironment surface in each well.

The sequences of the 20 peptide motifs include RGD, PHSRN-RGDSP (SEQ ID NO: 17), SPPRRARVT (SEQ ID NO: 18), TWYKIAF (SEQ ID NO: 45), RKRLQVQLSIRT (SEQ ID NO: 21), NRWHSIYITRFG (SEQ ID NO: 46), GIIFFL (SEQ ID NO: 50), RYVVLPR (SEQ ID NO: 51), RNIAEIKDI (SEQ ID NO: 48), WQPPRARI (SEQ ID NO: 19), KNNQKSEPLLIGRKKT (SEQ ID NO: 52), KKQRFRHRNRKGYRSG (SEQ ID NO: 53), LCCGRGHRTRTQRVTERCNC (SEQ ID NO: 39), LGTQGRLCNKTSEGMDGCEL (SEQ ID NO: 40), IVPLLLLVLH (SEQ ID NO: 41), YTAQGEPFPNNVEKLCAP (SEQ ID NO: 42), LFSHAVSSNG (SEQ ID NO: 54), ADTPPV (SEQ ID NO: 49), DQNDN (SEQ ID NO: 55), LRAHAVDING (SEQ ID NO: 56), and the like.

Experimental Results

Figure 8:
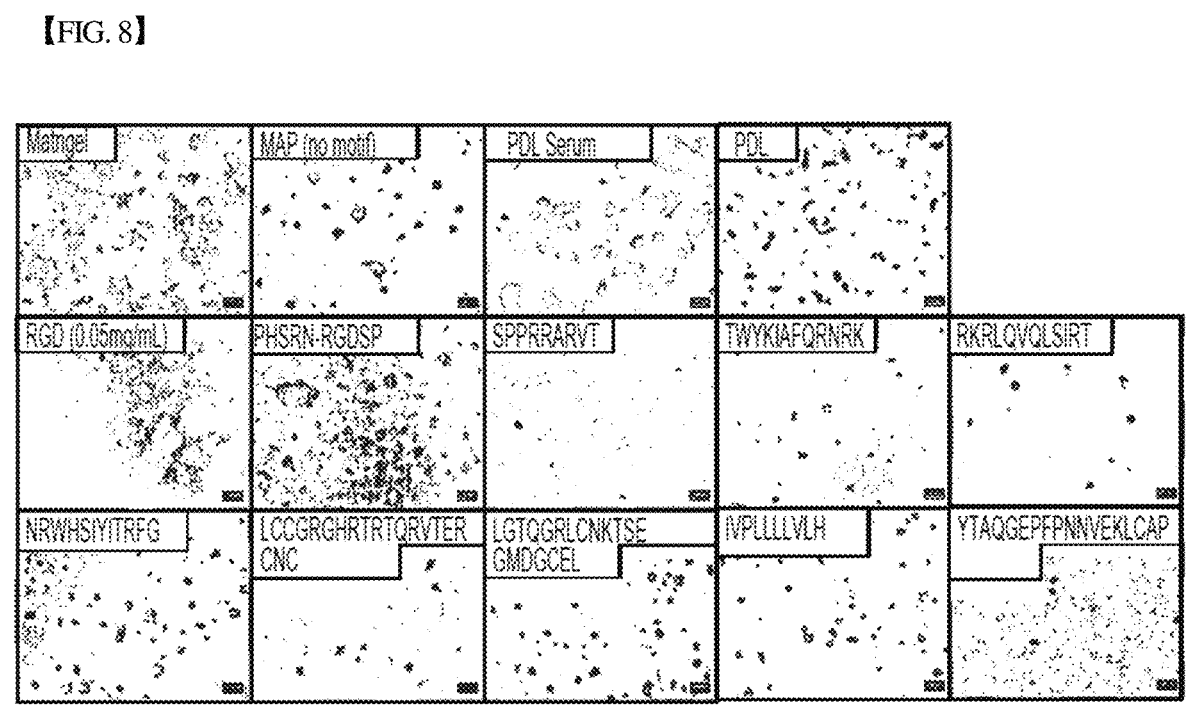
Figure 10A:
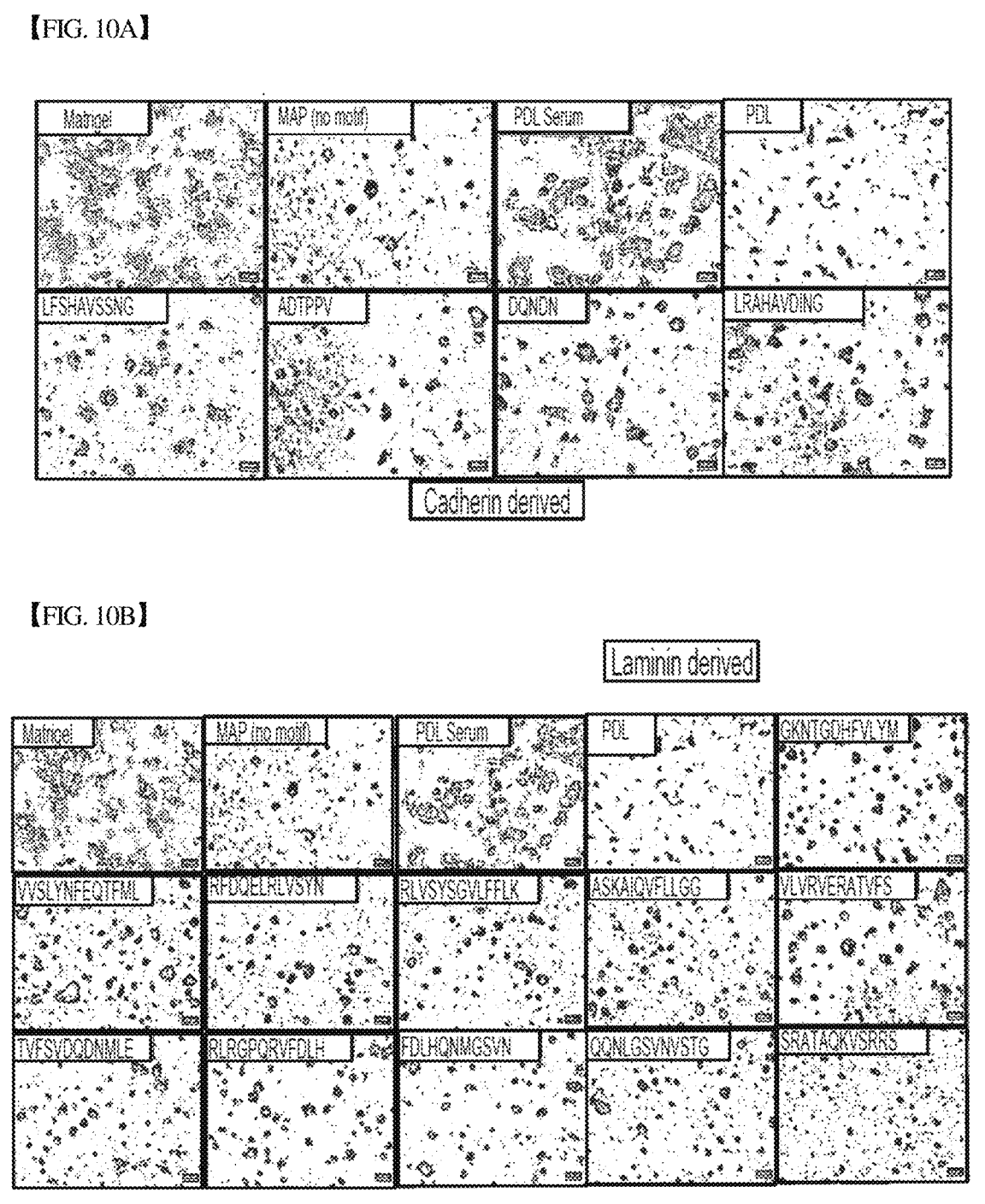

The experimental results are shown in FIGS. 8 to 10.

FIGS. 8 to 10 show results indicating that peptides derived from fibronectin (such as PHSRN-RGDSP (SEQ ID NO: 17)), laminin (such as RNIAEIKDI (SEQ ID NO: 48)) or cadherin (such as ADTPPV (SEQ ID NO: 49)) are effective for stem cell adhesion and colony formation.

As shown in the figures, it can be confirmed that peptides derived from fibronectin (such as PHSRN-RGDSP (SEQ ID NO: 17)), laminin (such as RNIAEIKDI (SEQ ID NO: 48)) or cadherin (such as ADTPPV (SEQ ID NO: 49)) are effective for stem cell adhesion and colony formation. However, PHSRN-RGDSP (SEQ ID NO: 17) resulted in the cell adhesion and colony size comparable to the levels of Matrigel, and thus PHSRN-RGDSP (SEQ ID NO: 17) was used in subsequent experiments.

Example 5: Effect of Peptide Motif on Culture of Stem Cells

Experimental Method

1) To investigate a microenvironment showing excellent embryonic stem cell self-renewal and growth by the use of the array prepared in Example 4, a cell culture experiment was performed.

2) A cell culture medium containing serum replacement medium and LIF was dispensed into each well, and then mouse-derived embryonic stem cells were cultured therein for 96 hours, after which the effect of each microenvironment on embryonic stem cell self-renewal and colony size was examined by AP staining.

To verify the effect of the peptide motif, nanofibers and a PDL-coated surface, which have no peptide motif, were used as controls in comparative experiments.

Experimental Results

The experimental results are shown in FIGS. 11 and 12.

FIG. 11 shows the results of AP staining performed to examine the effects of each motif on embryonic stem cell self-renewal and colony size.

The effect of each motif on embryonic stem cell self-renewal and colony size was examined by AP staining, and as a result, as shown in FIG. 11, it was confirmed that the nanofibers comprising the PHSRN-RGDSP (SEQ ID NO: 17) motif exhibited excellent self-renewal effects and the largest colony size.

FIG. 12 shows the effect of a coating method (2D plate coating) used for protein coating, and the experimental results are as follows.

Coated protein: 0.5 mg/ml Combo
  (A): a protein solution was immediately added and coated onto a NHS/EDC solution
  (R): a protein solution was coated after removal of a NHS/EDC solution.

As a result, in (A), the protein was observed as particles, but in (R), no particles were observed. In addition, in (A), a colony shape with well-maintained sternness was maintained during culture of the mESCs, but in (R), there were many differentiated cells with no sternness maintained. This suggests that the shape of the protein coated varies depending on the coating method and formation of the particles has a better effect on culture of the mESCs.

This experiment revealed that optimization of the type of peptide motif on the nanofiber surface and the topography of a surface for cell culture can greatly improve stem cell self-renewal and colony size.

Example 6: Effect of Combination of Cell Receptor Activation Motifs on Culture of Human Induced Pluripotent Stem Cells (1)

Experimental Method

According to Examples 1 and 2, membranes having a controlled nanofiber diameter of 200 nm were manufactured. At this time, the nanomembrane surface was prepared to have peptide motifs capable of simultaneously controlling the activities of three receptors (integrin-FGF receptor, integrin-Frizzled receptor and integrin-LIF receptor), in order to confirm the synergistic effect of combinations of peptides capable of simultaneously controlling different receptors, among the motifs confirmed to have an effect on stem cell culture in Example 5 among the seven key receptors that determine the behavior of stem cells.

Membranes with three microenvironments were prepared and coated on 6 well plates. Culture of human induced pluripotent stem cells was performed in the same manner as described in Example 5, and the effect of each microenvironment on the behavior of the stem cells was examined.

Experimental Results

The experimental results are shown in FIGS. 13 and 14.

FIGS. 13 and 14 show the results of AP staining performed to examine the effects of simultaneous control of activities of two key receptors on stem cell self-renewal and colony size.

Specifically, FIG. 13 shows the results obtained by coating PHSRN-RGDSP (SEQ ID NO: 17) and each FGF protein on plates and examining whether the coated protein can simultaneously control integrin-FGF receptor and examining the effect of the coating concentration of the proteins.

From the experimental results, it can be confirmed that the cell shape and the colony size were different between the plate was coated with PHSRN-RGDSP (SEQ ID NO: 17) alone and when the plate was coated with a combination of PHSRN-RGDSP (SEQ ID NO: 17) and each FGF protein. It can be seen that when the plate was coated with the FGF3 protein, the shape of the stem cells was better and the colony size increased, compared to when the plate was coated with FGF1 or FGF4. In addition, it can be seen that as the amount of protein coated increased, the colony size became smaller, but the shape of the stem cells became better. This suggests that coating with a combination of PHSRN-RGDSP (SEQ ID NO: 17) and the FGF3 protein has a better effect on the culture of human induced pluripotent stem cells than coating with PHSRN-RGDSP (SEQ ID NO: 17) alone.

In addition, as shown in FIGS. 14A to 14C, it can be confirmed that when integrin receptor and FGF receptor were simultaneously controlled, better self-renewal results than when integrin receptor alone was controlled could be obtained, and the cell shape and the colony size also approached those of the positive control Matrigel.

Comparison of the cell shape and the colony size indicated that control of integrin-Frizzed receptor and integrin-LIF receptor had a better effect than control of integrin-FGF receptor. Comparison of the stem cell shape and the colony size indicated that the self-renewal and growth/proliferation effects were better in the order of integrin-Frizzed receptor>integrin-LIF receptor>integrin-FGF receptor.

In particular, a combination of integrin-Frizzed receptor was above the Matrigel level in terms of the maintenance of stem cell differentiation potential and exhibited an effect similar to that of iMatrix.

From the experimental results, it could be confirmed in this Example that the seven receptors that determine the behavior of stem cells have different degrees of contribution to the maintenance of stem cell differentiation potential and the self-renewal of stem cells, and that when two receptors are simultaneously controlled, a combination of integrin receptor and Frizzled receptor is a mimetic which is closest to an in vivo microenvironment.

Example 7: Effect of Combination of Cell Receptor Activation Motifs on Culture of Human Induced Pluripotent Stem Cells (2)

Experimental Method

According to Example 6, plates having peptide motifs present on the surface thereof were prepared. At this time, the plate surface has a peptide motif that binds to each receptor so as to simultaneously control the activities of four receptors among the seven key receptors.

According to the same procedures as described in Examples 5 and 6, the effect of each microenvironment on culture of human induced pluripotent stem cells was examined.

Combinatorial receptors that are controlled by a surface coated on each well plate are integrin-Frizzed-FGF-TGFβ receptor, integrin-LIF-FGF-TGFβ, integrin-Frizzled-LIF-TGFβ, and integrin-Frizzled-LIF-FGF receptor.

Experimental Results

The experimental results are shown in FIGS. 15 and 16.

FIG. 15 shows the results of two-dimensionally examining the effect of protein motifs in hiPSC cells, and indicates the following:

Culture of hiPSCs after coating proteins on a 2D plate
Control: Matrigel

Proteins coated: Five proteins, Combo, FGF3, TGFb1, Wnt5a, and LIF1. "All" indicates coating with a mixture of all proteins (each protein was added at a concentration of 0.1 mg/ml). The symbol "-" indicates the protein excluded from the mixture solution (e.g., -FGF3 indicates that only FGF was excluded from the mixture solution of the five proteins).

*- indicates coating with Combo alone, and MAP indicates coating with 0.1 mg/ml Combo+0.4 mg/ml MAP.

From the experimental results, it was shown that when the plate was coated with Combo alone, all hiPSCs grew in a differentiated form, and when MAP was added, hiPSCs grew, but the colony size became smaller. In addition, in the absence of FGF3, the colony size became smaller, and in the absence of TGFb1 and Wnt5a, the colony size became larger, but a differentiated form appeared. In the absence of LIF, the colony shape became better, there was a difference in the effect of the protein motifs coated, and the colony shape of hiPSCs also changed due to the addition of the protein motifs.

In addition, FIG. 16 shows the results of two-dimensionally examining the effects of protein motifs in hiPSCs. Specifically, it shows the results of analyzing the expression of sternness markers after coating proteins on 2D plates and culturing hiPSCs, and indicates the following:

Control: Matrigel

Proteins coated: Five proteins, Combo, FGF3, TGFb1, Wnt5a, and LIF1. "All" indicates coating with a mixture of all proteins (each protein was added at a concentration of 0.1 mg/ml). The symbol "-" indicates the protein excluded from the mixture solution (e.g., -FGF3 indicates that only FGF was excluded from the mixture solution of the five proteins).

*- indicates coating with Combo alone, and MAP indicates coating with 0.1 mg/ml Combo+0.4 mg/ml MAP.

It shows the results of analyzing the expression of sternness markers (Oct4 and Sox2) in hiPSCs, and indicates the following.

From the experimental results, it can be seen that when the plate was coated with Combo alone, the cells adhered at a level similar to the level of Matrigel, but the expression of sternness markers was weak, and when the plate was coated with a mixture of Combo and the motifs, the expression of sternness markers was stronger than that of Matrigel, and when FGF3 was absent, the colony shape of hiPSCs became smaller and the expression of sternness markers became weaker. In addition, it was confirmed that when TGFb1 and Wnt5a were absent, the expression of sternness markers became weaker, and coating with the motif mixture was effective for maintaining the sternness of hiPSCs, and the shape of the cells and the expression of sternness markers varied depending on the type of motif used.

As mentioned in Example 6, the seven receptors had different degrees of contribution to stem cell self-renewal. In addition, comparison of the combination of four receptors of this Example with the combination of two receptors indicated that the combination of four receptors exhibited better results than the combination of two receptors.

When the degree of contribution of each receptor was examined, it can be seen that the degree of contribution of LIF receptor was the lowest, and the degree of contribution of FGF receptor was higher than that of LIF receptor but lower than that of Frizzled or TGF receptor. In particular, it can be seen that the combination containing Frizzled or TGF receptor had a better self-renewal effect than Matrigel and had an effect comparable to the level of iMatrix.

Example 8. Effect of Different Physical Environments on Culture of Human Induced Pluripotent Stem Cells (3)

Experimental Method

According to Examples 1 and 2, membranes having nanofiber diameters of 200 nm (Combo-A type), 600 nm (Combo-B type) and 1000 nm (Combo-C type) were prepared. At this time, the membrane surface had PHSRN-RGDSP (SEQ ID NO: 17) which is an integrin binding peptide motif.

According to the same procedures as described in Examples 6 and 7, the effect of each microenvironment on culture of human induced pluripotent stem cells was examined.

Experimental Results

The experimental results are shown in FIG. 17.

In order to examine the effect of the diameter of nanofibers on stem cell culture, the AP staining results shown in FIG. 17 were analyzed. As a result, as the diameter increased, the stem cell adhesion and colony size increased. It can be seen that in the nanofibers having the same diameter, the number of cells adhered and the colony size increased as the density of PHSRN-RGDSP (SEQ ID NO: 17) increased. Specifically, FIG. 17 indicates the following.

Control of fiber diameter of PVDF membrane
Blend-spun protein: 10 mg/ml Combo
PVDF (having no protein)
Combo blend spinning A type: fiber diameter of 200 nm
Combo blend spinning B type: fiber diameter of 600 nm
Combo blend spinning C type: fiber diameter of 1000 nm.

From the experimental results, it could be confirmed that when A, B and C type Combo motifs were included, cell adhesion increased, and cell adhesion did differ depending on the fiber diameter. In addition, the degree of adhesion indicated A=B<C. (in FIG. 17, Combo blend spinning A, B and C type membranes).

Referring to FIG. 17, it can be seen that when mESCs were cultured in the membrane obtained by Combo blend spinning, a larger number of cells adhered and grew as the fiber diameter increased, and the colony shape of mESCs in the membrane obtained by Combo blend spinning was better than that in PDL used as the control. In conclusion, it can be seen that the sternness of mESCs was well maintained.

It can be seen that an increasing nanofiber diameter is advantageous for maintaining the self-renewal and differential potential of stem cells.

Example 9. Effect of Density of Integrin Binding Motif (i)

Experimental Method

In order to examine the effect of the density of the integrin-binding motif PHSRN-RGDSP (SEQ ID NO: 17) in the nanofiber surface on culture of stem cells, the extracellular matrix mimetic MAPTrix™ PHSRN-RGDSP (SEQ ID NO: 17) was used in amounts of 10 mg and 20 mg when manufacturing nanofibers according to Example 1, so that the density of PHSRN-RGDSP (SEQ ID NO: 17) in the nanofiber surface changed. The effect of the density of PHSRN-RGDSP (SEQ ID NO: 17) on the self-renewal and colony size of stem cells was examined.

Experimental Results

The experimental results are shown in FIG. 18. FIG. 18 shows the results of examining the effect of the density of a PHSRN-RGDSP (SEQ ID NO: 17) motif in mESCs. Detailed experimental conditions and results are as follows:

The protein was added in amounts of 10 mg and 20 mg when manufacturing Combo blend-spun B type membranes according to Examples 1 and 2, and then mESCs were cultured on the membranes and the colony size and shape of the mESCs were examined.

Control: PDL
Blend-spun protein motif: 10 mg PHSRN-RGDSP (SEQ ID NO: 17), and 20 mg PHSRN-RGDSP (SEQ ID NO: 17)

As can be seen in FIG. 18, as the surface density of PHSRN-RGDSP (SEQ ID NO: 17) increased, the adhesion of stem cells and the colony size also increased. Namely, the surface density of PHSRN-RGDSP (SEQ ID NO: 17) plays an important role in the self-renewal and growth of stem cells. However, it can be seen that the self-renewal is still at a lower level than self-renewal on PDL. In order to confirm the surface density corresponding to the level on PDL, an additional experiment was performed, and the contents thereof will be addressed in Example 10 (Effect of Density of Integrin Binding Motif (ii)) below.

It can be seen that the membrane showed lower self-renewal than that of PDL which is a common material for stem cell culture, but when the density of PHSRN-RGDSP (SEQ ID NO: 17) was increased, the effect of improving self-renewal could be obtained.

Example 10: Effect of Density of Integrin Binding Motif (ii)

Experimental Method

In order to further examine the effect of the density of the integrin binding motif PHSRN-RGDSP (SEQ ID NO: 17) on culture of stem cells, a PHSRN-RGDSP (SEQ ID NO: 17) mimetic was coated on the 2D plate surface using an EDC/NHS catalyst, and the effect of the concentration (i.e., surface density) of PHSRN-RGDSP (SEQ ID NO: 17) on the behavior of stem cells was examined according to the procedures described in Examples 6 and 7. The concentrations of PHSRN-RGDSP (SEQ ID NO: 17) in the coating solution were 0.01 mg/ml, 0.06 mg/ml, 0.1 mg/ml, 0.5 mg/ml, and 1 mg/ml, respectively.

Experimental Results

The experimental results are shown in FIG. 19. FIG. 19 shows the effect of protein coating concentration on hiPSC culture (2D plate), and an experiment for examining the effect was performed under the following conditions.

Control: Matrigel
Coated protein: MAP and Combo
Coating concentration: 0.01 mg/ml, 0.06 mg/ml, 0.1 mg/ml, 0.5 mg/ml, and 1 mg/ml.

Referring to FIG. 19, it can be seen that when the plate was coated with MAP, hiPSCs hardly adhered, and when the plate was coated with 0.5 mg/ml of MAP, cells adhered and grew, but did not form a normal colony, and when the plate was coated with Combo, hiPSCs adhered and grew, and as the concentration of Combo increased, a larger number of cells adhered and grew, similar to growth on Matrigel. In addition, it can be seen that the coating concentration of the protein affected the culture of hiPSCs and the motif (Combo) was effective.

It was confirmed that as the coating concentration of PHSRN-RGDSP (SEQ ID NO: 17), that is, the density of PHSRN-RGDSP (SEQ ID NO: 17) on the surface, increased, the adhesion of cells increased and the colony size also increased. As observed in the AP staining results shown in FIG. 19, it can be seen that when the coating concentration of PHSRN-RGDSP (SEQ ID NO: 17) was 0.1 mg/mL or higher, the cell adhesion performance and colony size comparable to the levels observed on Matrigel were obtained.

The minimum concentration for obtaining the self-renewal and growth effects comparable to the levels observed on Matrigel was examined, and the obtained result could be used as an index to determine the minimum concentration for simultaneously controlling the activities of key integrin receptors.

Example 11: Measurement of the Effect of Nanomembrane Thickness on Stem Cell Self-Renewal (the Above-Described Conditions were Maintained Except for the Thickness)

Experimental Method

According to Examples 1 and 2, membranes having nanofiber diameters of 600 nm and 1000 nm were manufactured. During the manufacture, the thicknesses of the membranes were controlled. The membranes having a fiber diameter of 600 nm were manufactured to have thicknesses of 1.5 μm, 2.8 μm and 5.5 μm, and the membranes having a fiber diameter of 1000 nm were manufactured to have thicknesses of 3 μm, 5 μm and 7 μm. At this time, the membranes were manufactured by blend-spinning with PHSRN-RGDSP (SEQ ID NO: 17). The behavior of stem cells depending on the thickness of the membrane was examined according to the procedures described in Example 5.

Experimental Results

The experimental results are shown in FIG. 20. FIG. 20 shows the results of controlling the thicknesses of PVDF membranes, and the experimental conditions and results are as follows:

Blend-spun protein: 10 mg/ml Combo
Combo blend-spun B type: fiber diameter of 600 nm
Combo blend-spun C type: fiber diameter of 1 μm.

From the experimental results, it can be seen that when the B or C type Combo motif was included, the cell adhesion increased, and the cell adhesion did differ depending on the thickness of the membrane. In addition, the adhesion was higher in the order of B<C. At the same time, the effect of the membrane thickness on the behavior of stem cells was examined by AP staining.

From the experimental results, it can be seen that in all the membranes having nanofiber diameters of 600 nm and 1000 nm, the self-renewal efficiency did differ depending on the membrane thickness, and as the membrane thickness became thicker, the number of stem cells increased.

In addition, the experimental results revealed that as the membrane thickness became thicker, the effect of stem cell culture was better.

Example 12: Cell Migration Assay

Experimental Method

According to Examples 1 and 2, nanofiber membranes having a fiber diameter of 200 nm were manufactured. In order to explore microenvironments suitable for the growth and migration of the epithelial HaCaT (keratinocyte) and HS27 (fibroblast) cells constituting skin tissue, four laminin-derived peptide motifs and four collagen-derived peptide motifs were prepared, and 16 microenvironments containing the growth factor basic FGF and FGF mimetic peptide were prepared on surfaces coated with each motif. FIG. 21 shows a microenvironment array comprising individual motifs alone. Using this array, HaCaT and HS27 cells were dispensed, and microenvironments effective for cell growth and migration were explored.

The effect of each microenvironment on the migration of epithelial cells was examined by a scratch test.

Experimental Results

The experimental results are shown in FIGS. 22 to 24. FIG. 22 is a graph showing the effect of each peptide motif on the migration of cells, and as can be seen therein, the effect of the laminin-derived peptide motifs was better than that of the collagen-derived peptide motifs. In addition, it can be seen that there is an optimal concentration of each motif at which the migration reaches the maximum.

However, as can be seen in FIG. 24, the microenvironments containing the growth factor has resulted in promoting overall cell migration. In addition, it can be seen that, in the microenvironments containing the growth factor FGF, the difference in the effect of the collagen- or laminin-derived peptide motifs is offset.

FIG. 23 shows the representative results of a scratch test, and the degree of cell migration with the passage of time can be seen therein. In FIG. 23A, the collagen-derived motif GLPGER (SEQ ID NO: 59) shows a low effect on cell migration. However, in FIG. 23B, the laminin-derived motif IKVAV (SEQ ID NO: 60) shows a high effect on cell migration.

The migration of epithelial cells is essential for the wound healing process, and when a microenvironment that optimizes the migration of each type of cell is realized, the wound healing time may be shortened. The present disclosure may provide a microenvironment that optimizes the migration of each type of cells, and thus may be used for the development of wound dressing materials, etc.

[Sequence List Text]

SEQ ID NO: 1
model peptide of the tandem repeat decapeptide derived from foot protein 1 (14P-1, *Mytilus edulis*):
Ala Lys Pro Ser Tyr Pro Pro Thr Tyr Lys SEQ ID NO: 2
2 times repeated sequence derived from foot protein 1 (1-P-1, *Mytilus edulis*):
Ala Lys Pro Ser Tyr Pro Pro Thr Tyr Lys Ala Lys Pro Ser Tyr Pro Pro Thr Tyr Lys SEQ ID NO: 3
6 times repeated sequence derived from foot protein 1 (1-P-1, *Mytilus edulis*):
Ala Lys Pro Ser Tyr Pro Pro Thr Tyr Lys Ala Lys Pro Ser TyrPro Pro Thr Tyr Lys Ala Lys Pro
Ser Tyr Pro Pro Thr Tyr LysAla Lys Pro Ser Tyr Pro Pro Thr Tyr Lys Ala Lys Pro Ser TyrPro Pro
Thr Tyr Lys Ala Lys Pro Ser Tyr Pro Pro Thr Tyr Lys

[Sequence List Text]

SEQ ID NO: 4
partial sequence of foot protein type 2 (FP-2, *Mytilus californianus*):
Glu Val His Ala Cys Lys Pro Asn Pro Cys Lys Asn Asn Gly ArgCys Tyr Pro Asp Gly Lys Thr
Gly Tyr Lys Cys Lys Cys Val Gly Gly Tyr Ser Gly Pro Thr Cys Ala Cys SEQ ID NO: 5
Foot protein type 3 (FP-3, *Mytilus edulis*):
Ala Asp Tyr Tyr Gly Pro Lys Tyr Gly Pro Pro Arg Arg Tyr Gly Gly Gly Asn Tyr Asn Arg Tyr
Gly Gly Ser Arg Arg Tyr Gly Gly Tyr Lys Gly Trp Asn Asn Gly Trp Lys Arg Gly Arg Trp Gly
Arg Lys Tyr Tyr Glu Phe Glu Phe SEQ ID NO: 6
Foot protein type 3 (FP-3, *Mytilus galloprovincialis*: mgfp-3A):
Ala Asp Tyr Tyr Gly Pro Lys Tyr Gly Pro Pro Arg Arg Tyr Gly Gly Asn Tyr Asn Arg Tyr
Gly Arg Arg Tyr Gly Gly Tyr Lys Gly Trp Asn Asn Gly Trp Lys Arg Gly Arg Trp Gly Arg Lys
Tyr Tyr SEQ ID NO: 7
partial sequence from foot protein type 4 (*Mytilus californianus*):
Gly His Val His Arg His Arg Val Leu His Lys His Val His Asn His Arg Val Leu His Lys His
Leu His Lys His Gln Val Leu His Gly His Val His Arg His Gln Val Leu His Lys His Val His Asn
His Arg Val Leu His Lys His Leu His Lys His Gln Val Leu His SEQ ID NO: 8
Foot protein type5 (FP-5, *Mytilus edulis*):
Ser Ser Glu Glu Tyr Lys Gly Gly Tyr Tyr Pro Gly Asn Ala Tyr His Tyr His Ser Gly Gly Ser Tyr
His Gly Ser Gly Tyr His Gly Gly Tyr Lys Gly Lys Tyr Tyr Gly Lys Ala Lys Lys Tyr Tyr Tyr Lys
Tyr Lys Asn Ser Gly Lys Tyr Lys Tyr Leu Lys Lys Ala Arg Lys Tyr His Arg Lys Gly Tyr Lys
Lys Tyr Tyr Gly Gly Ser Ser SEQ ID NO: 9
Foot protein 5 (FP-5, *Mytilus edulis*):
Ser Ser Glu Glu Tyr Lys Gly Gly Tyr Tyr Pro Gly Asn Thr Tyr His Tyr His Ser Gly Gly Ser Tyr
His Gly Ser Gly Tyr His Gly Gly Tyr Lys Gly Lys Tyr Tyr Gly Lys Ala Lys Lys Tyr Tyr Tyr Lys
Tyr Lys Asn Ser Gly Lys Tyr Lys Tyr Leu Lys Lys Ala Arg Lys Tyr His Arg Lys Gly Tyr Lys
Lys Tyr Tyr Gly Gly Gly Ser Ser SEQ ID NO: 10
Foot protein 5 (FP-5, *Mytilus coruscus*):
Tyr Asp Asp Tyr Ser Asp Gly Tyr Tyr Pro Gly Ser Ala Tyr Asn Tyr Pro Ser Gly Ser His Trp His
Gly His Gly Tyr Lys Gly Lys Tyr Tyr Gly Lys Gly Lys Tyr Tyr Lys Phe Lys Arg Thr
Gly Lys Tyr Lys Tyr Leu Lys Lys Ala Arg Lys Tyr His Arg Lys Gly Tyr Lys Lys His Tyr Gly
Gly Ser Ser Ser SEQ ID NO: 11
mussel adhesive protein foot protein type5 from (*Mytilus galloprovincialis*):
Ser Ser Glu Glu Tyr Lys Gly Gly Tyr Tyr Pro Gly Asn Thr Tyr His Tyr His Ser Gly Gly Ser Tyr
His Gly Ser Gly Tyr His Gly Gly Tyr Lys Gly Lys Tyr Tyr Gly Lys Ala Lys Lys Tyr Tyr Tyr Lys
Tyr Lys Asn Ser Gly Lys Tyr Lys Tyr Leu Lys Lys Ala Arg Lys Tyr His Arg Lys Gly Tyr Lys
Lys Tyr Tyr Gly Gly Gly Ser Ser SEQ ID NO: 12
mussel adhesive protein foot protein type 6:
Gly Gly Gly Asn Tyr Arg Gly Tyr Cys Ser Asn Lys Gly Cys Arg Ser Gly Tyr Ile Phe Tyr Asp
Asn Arg Gly Phe Cys Lys Tyr Gly Ser Ser Ser Tyr Lys Tyr Asp Cys Gly Asn Tyr Ala Gly Cys
Cys Leu Pro Arg Asn Pro Tyr Gly Arg Val Lys Tyr Tyr Cys Thr Lys Lys Tyr Ser Cys Pro Asp
Asp Phe Tyr Tyr Tyr Asn Asn Lys Gly Tyr Tyr Tyr Asn Asp Lys Asp Tyr Phe Asn Cys Gly
Ser Tyr Asn Gly Cys Cys Leu Arg Ser Gly Tyr SEQ ID NO: 13
hybrid mussel adhesive protein (FP-151, MEFP-5 based:Kollodis)
Ala Lys Pro Ser Tyr Pro Pro Thr Tyr Lys Ala Lys Pro Ser Tyr Pro Pro Thr Tyr Lys Ala Lys Pro
Ser Tyr Pro Pro Thr Tyr Lys Ala Lys Pro Ser Tyr Pro Pro Thr Tyr Lys Ala Lys Pro Ser Tyr Pro
Pro Thr Tyr Lys Ala Lys Pro Ser Tyr Pro Pro Thr Tyr Lys Ser Ser Glu Glu Tyr Lys Gly Gly Tyr
Tyr Pro Gly Asn Ala Tyr His Tyr His Ser Gly Gly Ser Tyr His Gly Ser Gly Tyr His Gly Gly Tyr
Lys Gly Lys Tyr Tyr Gly Lys Ala Lys Lys Tyr Tyr Tyr Lys Tyr Lys Asn Ser Gly Lys Tyr Lys Tyr
Leu Lys Lys Ala Arg Lys Tyr His Arg Lys Gly Tyr Lys Tyr Gly Gly Ser Ser Ala Lys Pro Ser
Tyr Pro Pro Thr Tyr Lys Ala Lys Pro Ser Tyr Pro Pro Thr Tyr Lys Ala Lys Pro Ser Tyr Pro Pro
Thr Tyr Lys Ala Lys Pro Ser Tyr Pro Pro Thr Tyr Lys Ala Lys Pro Ser Tyr Pro Pro Thr Tyr Lys
Ala Lys Pro Ser Tyr Pro Pro Thr Tyr Lys SEQ ID NO: 14
hybrid mussel adhesive protein (FP-151, MGFP-5 based)
Ala Lys Pro Ser Tyr Pro Pro Thr Tyr Lys Ala Lys Pro Ser Tyr Pro Pro Thr Tyr Lys Ala Lys Pro
Ser Tyr Pro Pro Thr Tyr Lys Ala Lys Pro Ser Tyr Pro Pro Thr Tyr Lys Ala Lys Pro Ser Tyr Pro
Pro Thr Tyr Lys Ala Lys Pro Ser Tyr Pro Pro Thr Tyr Lys Ser Ser Glu Glu Tyr Lys Gly Gly Tyr

```
Tyr Pro Gly Asn Thr Tyr His Tyr His Ser Gly Gly Ser Tyr His Gly Ser Gly Tyr His Gly Gly Tyr
Lys Gly Lys Tyr Tyr Gly Lys Ala Lys Lys Tyr Tyr Lys Tyr Lys Asn Ser Gly Lys Tyr Lys Tyr
Leu Lys Lys Ala Arg Lys Tyr His Arg Lys Lys Gly Lys Lys Tyr Lys Tyr Gly Gly Gly Ser Ser Ala Lys
Pro Ser Tyr Pro Pro Thr Tyr Lys Ala Lys Pro Ser Tyr Pro Pro Thr Tyr Lys Ala Lys Pro Ser Tyr
Pro Pro Thr Tyr Lys Ala Lys Pro Ser Tyr Pro Pro Thr Tyr Lys Ala Lys Pro Ser Tyr Pro Pro Thr
Tyr Lys Ala Lys Pro Ser Tyr Pro Pro Thr Tyr Lys
```

SEQ ID NO: 15

Fibronectin-derived peptide (RGD):
Arg Gly Asp

SEQ ID NO: 16

Fibronectin-derived peptide (GRGDSP):
Gly Arg Gly Asp Ser Pro

SEQ ID NO: 17

Fibronectin-derived peptide (PHSRN-RGDSP):
ProH is Ser Arg Asn Arg Gly Asp Ser Pro

SEQ ID NO: 18

Fibronectin-derived peptide (SPPRRARVT):
Ser Pro Pro Arg Arg Ala Arg Val Thr

SEQ ID NO: 19

Fibronectin-derived peptide (WQPPRARI):
Trp Gln Pro Pro Arg Ala Arg Ile

SEQ ID NO: 20

Fibronectin-derived peptide (KNNQKSEPLIGRKKT)
Lys Asn Asn Gln Lys Ser Glu Pro Leu Ile Gly Arg Lys Lys Thr

SEQ ID NO: 21

Laminin-derived peptide (RKRLQVQLSIRT):
Arg Lys Arg Leu Gln Val Gln Leu Ser Ile Arg Thr

SEQ ID NO: 22

Laminin-derived peptide (GKNTGDHFVLYM):
Gly Lys Asn Thr Gly Asp His Phe Val Leu Tyr Met

SEQ ID NO: 23

Laminin-derived peptide (VVSLYNFEQTFML):
Val Val Ser Leu Tyr Asn Phe Glu Gln Thr Phe Met Leu

SEQ ID NO: 24

Laminin-derived peptide (RFDQELRLVSYN):
Arg Phe Asp Gln Glu Leu Arg Leu Val Ser Tyr Asn

SEQ ID NO: 25

Laminin-derived peptide (RLVSYSGVLFFLK):
Arg Leu Val Ser Tyr Ser Gly Val Leu Phe Phe Leu Lys

SEQ ID NO: 26

Laminin-derived peptide (ASKAIQVFLLGG):
Ala Ser Lys Ala Ile Gln Val Phe Leu Leu Gly Gly

SEQ ID NO: 27

Laminin-derived peptide (VLVRVERATVFS):
Thr His Arg Pro Pro Met Trp Ser Pro Val Trp Pro

SEQ ID NO: 28

Laminin-derived peptide (TVFSVDQDNMLE):
Thr Val Phe Ser Val Asp Gln Asp Asn Met Leu Glu

SEQ ID NO: 29

Laminin-derived peptide (RLRGPQRVFDLH):
Arg Leu Arg Gly Pro Gln Arg Val Phe Asp Leu His

SEQ ID NO: 30

Laminin-derived peptide (FDLHQNMGSVN):
Phe Asp Leu His Gln Asn Met Gly Ser Val Asn

SEQ ID NO: 31

Laminin-derived peptide (QQNLGSVNVSTG):
Gln Gln Asn Leu Gly Ser Val Asn Val Ser Thr Gly

[Sequence List Text]

Laminin-derived (SRATAQKVSRRS):  
SEQ ID NO: 32  
Ser Arg Ala Thr Ala Gln Lys Val Ser Arg Arg Ser FGF-derived peptide (ANRYLAMKEDGRLLAS):  
SEQ ID NO: 33  
Ala Asn Arg Tyr Leu Ala Met Lys Glu Asp Gly Arg Leu Leu Ala Ser FGF-derived peptide (HFKDPKRLYCK):  
SEQ ID NO: 34  
His Phe Lys Asp Pro Lys Arg Leu Tyr Cys Lys FGF-derived peptide (FLPMSAKS):  
SEQ ID NO: 35  
Phe Leu Pro Met Ser Ala Lys Ser FGF-derived peptide (KTGPGQKA):  
SEQ ID NO: 36  
Lys Thr Gly Pro Gly Gln Lys Ala TGF-derived peptide (LTGKNFPMFHRN):  
SEQ ID NO: 37  
Leu Thr Gly Lys Asn Phe Pro Met Phe His Arg Asn TGF-derived peptide (MHRMPSFLPTTL):  
SEQ ID NO: 38  
Met His Arg Met Pro Ser Phe Leu Pro Thr Thr Leu WNT-derived peptide (LCCGRGHRTRTQRVTERCNC):  
SEQ ID NO: 39  
Leu Cys Cys Gly Arg Gly His Arg Thr Arg Thr Gln Arg Val Thr Glu Arg Cys Asn Cys WNT-derived peptide (LGTQGRLCNKTSEGMDGCEL):  
SEQ ID NO: 40  
Leu Gly Thr Gln Gly Arg Leu Cys Asn Lys Thr Ser Glu Gly Met Asp Gly Cys Glu Leu LIF-derived peptide (IVPLLLLVLH):  
SEQ ID NO: 41  
Ile Val Pro Leu Leu Leu Val Leu His LIF-derived peptide (YTAQGEPFPNNVEKLCAP):  
SEQ ID NO: 42  
Tyr Thr Ala Gln Gly Glu Pro Phe Pro Asn Asn Val Glu Lys Leu Cys Ala Pro Fibronectin-derived peptide (KLDAPT):  
SEQ ID NO: 43  
Lys Leu Asp Ala Pro Thr Fibronectin-derived peptide (EILDVPSTT):  
SEQ ID NO: 44  
Glu Ile Leu Asp Val Pro Ser Thr Thr Laminin-derived peptide (TWYKIAFQRNRK):  
SEQ ID NO: 45  
Thr Trp Tyr Lys Ile Ala Phe Gln Arg Asn Arg Lys Laminin-derived peptide (NRWHSIYITRFG):  
SEQ ID NO: 46  
Asn Arg Trp His Ser Ile Tyr Ile Thr Arg Phe Gly

PRIOR ART DOCUMENTS

Patent Documents

Patent Document 1: US Patent Publication No. 2006-0134050

The invention claimed is:

1. A surface for controlling cell behavior, the surface comprising two or more peptide motifs, including a P1 (first peptide) motif and a P2 (second peptide) motif, which bind to cell receptors, wherein the peptide motifs bind to two or more different receptors on the cell,
   wherein the P1 (first peptide) motif comprises SEQ ID NO: 17,
   wherein the P2 (second peptide) motif is selected from the group consisting of SEQ ID NO: 40 and SEQ ID NO: 41.

2. The surface of claim 1, wherein the surface is a porous surface, a non-porous surface, or a combination thereof.

3. The surface of claim 1, wherein the surface is the surface of one or more of a nanofiber, a hydrogel and a particle.

4. The surface of claim 1, wherein the cell behavior is one or more selected from the group consisting of cell adhesion, migration, growth, proliferation, morphogenesis, differentiation and apoptosis.

* * * * *